US008168438B2

(12) United States Patent
Zamborini et al.

(10) Patent No.: US 8,168,438 B2
(45) Date of Patent: May 1, 2012

(54) CHEMICAL SENSORS FOR DETECTING HYDROGEN AND METHODS OF USE

(75) Inventors: Francis P. Zamborini, Louisville, KY (US); Francisco J. Ibanez, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 12/279,936

(22) PCT Filed: Jul. 26, 2008

(86) PCT No.: PCT/US2008/071276
§ 371 (c)(1),
(2), (4) Date: Aug. 19, 2008

(87) PCT Pub. No.: WO2009/015379
PCT Pub. Date: Jan. 29, 2009

(65) Prior Publication Data
US 2010/0224507 A1   Sep. 9, 2010

Related U.S. Application Data

(60) Provisional application No. 60/952,125, filed on Jul. 26, 2007.

(51) Int. Cl.
*G01N 33/00* (2006.01)
(52) U.S. Cl. ............. 436/124; 436/144; 422/90; 422/98
(58) Field of Classification Search ................... 436/124, 436/144; 422/90, 98
See application file for complete search history.

(56) References Cited

U.S. PATENT DOCUMENTS

| 5,186,860 | A | 2/1993 | Joyce, Jr. et al. |
| 5,879,631 | A | 3/1999 | Wewers et al. |
| 6,134,946 | A * | 10/2000 | Liu et al. ...................... 73/31.06 |
| 6,537,498 | B1 * | 3/2003 | Lewis et al. ................ 422/82.01 |
| 2005/0079551 | A1 | 4/2005 | Mizuno et al. |
| 2005/0245753 | A1 | 11/2005 | Cruse et al. |
| 2006/0014005 | A1 * | 1/2006 | Basco et al. .................. 428/209 |
| 2007/0240491 | A1 | 10/2007 | Pavlovsky et al. |

OTHER PUBLICATIONS

Ahn et al., "Easy Synthesis and Magnetic Properties of Iron Oxide Nanoparticles," Chem. Mater., 16, 2004, pp. 3274-3278.
Albert et al., "Cross-Reactive Chemical Sensor Arrays," Chem. Rev., 100, 2000, pp. 2595-2626.
Ananikov et al., "New Approach for Size- and Shape-Controlled Preparation of Pd Nanoparticles with Organic Ligands, Synthesis and Application in Catalysis," J. Am. Chem. Soc., 129, 2007, pp. 7252-7253.
Bevenot et al., "Hydrogen leak detection using an optical fibre sensor for aerospace applications," Sens. Actuators B, 67, 2000, 57-67.

(Continued)

*Primary Examiner* — Jill Warden
*Assistant Examiner* — Monique Cole
(74) *Attorney, Agent, or Firm* — Stites & Harbison PLLC; Terry L. Wright

(57) ABSTRACT

The presently-disclosed subject matter provides sensors and methods for detecting hydrogen by determining the conductivity of a chemiresistant film upon exposure to hydrogen, including for example chemiresistant films comprised of alkylamine-, alkylthiolate-, and/or surfactant-coated metal alloy nanoparticles.

29 Claims, 10 Drawing Sheets

OTHER PUBLICATIONS

Bonne et al., "N-Acylureido Functionality as Acceptor Substituent in Solvatochromic Fluorescence Probes: Detection of Carboxylic Acids, Alcohols, and Fluoride ions," J. A. Chem. Soc. 127, 2005, pp. 17158-17159.

Briglin et al., "Detection of Organic Mercaptan Vapors Using Thin Films of Alkylamine-Passivated Gold Nanocrystals," Langmuir., 20, 2004, pp. 299-305.

Brust et al., Self-Assembled Gold Nanoparticle Thin Films with Nonmetallic Optical and Electronic Properties, Langmuir., 14, 1998, pp. 5425-5429.

Brust et al., "Synthesis of Thiol-derivatised Gold Nanoparticles in a Two-phase Liquid-Liquid System," Chem. Comm., 7, 1994, pp. 801-802.

Cai et al., "Dual-Chemiresistor GC Detector Employing Monolayer-Protected Metal Nanocluster Interfaces," Anal. Chem., 74, 2002, pp. 3533-3539.

Cao et al., "Breath Analysis: Potential for Clinical Diagnosis and Exposure Assessment," Clin. Chem., 52, 2006, pp. 800-811.

Che et al., "Carbon nanotubule membranes for electrochemical energy storage and production," Nature, 393, 1998, pp. 346-349.

Choi et al., "Dynamics of CO2-Plasticized Electron Transport in Au Nanoparticle Films: Opposing Effects of Tunneling Distance and Local Site Mobility," J. Phys. Chem., 111, 2007, pp. 3778-3785.

Christofides et al., "Solid-state sensors for trace hydrogen gas detection," J. Appl. Phys. 68, 1990, pp. 1-30.

Crooks et al., "New Organic Materials Suitable for Use in Chemical Sensor Arrays," Acc. Chem. Res., 31, 1998, pp. 219-227.

Dankert et al., "Hydrogen-induced percolation in discontinuous films," Appl. Phys. Lett, 81, 2002, pp. 1618-1620.

David et al., "Molecular-wire behaviour in p-phenylenevinylene oligomers," Nature, 396, 1998, pp. 60-63.

Drew et al., "An Electronic Nose Transducer Array of Vapoluminescent Platinum(II) Double Salts," J. Am. Chem. Soc., 123, 2001, pp. 8414-8415.

Dutta et al., "Tea quality prediction using a tin oxide-based electronic nose: an artificial intelligence approach," Sens. Actuators B, 94, 2003, pp. 228-237.

Dwivedi et al., "Sensing properties of palladium-gate MOS (Pd-MOS) hydrogen sensor-based on plasma grown silcone dioxide," Sens. Actuators B, 71, 2000, pp. 161-168.

Eklund et al., "Synthesis and Catalytic Properties of Soluble Platinum Nanoparticles Protected by a Thiol Monolayer," Langmuir, 20, 2004, pp. 6012-6018.

Evans et al., "Vapour sensing using hybrid organic-inorganic nanostructured materials," Mater. Chem., 10, 2000, pp. 183-188.

Favier et al., "Hydrogen Sensors and Switches from Electrodeposited Palladium Mesowire Arrays," Science, 293, 2001, pp. 2227-2231.

Finlayson-Pitts et al., "Tropospheric Air Pollution: Ozone, Airobrne Toxics, Polycyclic Aromatic Hydrocarbons, and Particles," Science, 276, 1997, p. 1045-1052.

Foos et al., "Thiol-Terminated Di-, Tri-, and Tetraethylene Oxide Functionalized Gold Nanoparticles: A Water-Soluble, Charge-Neutral Cluster," Chem. Mater., 14, 2002, pp. 2401-2408.

Ganesan et al., "Monodisperse Thioether-Stabilized Palladium Nanoparticles: Synthesis, Characterization, and Reactivity," Chem. Mater., 19(14), 2007, pp. 3464-3471.

Gopel, W, "Chemical imaging: I. Concepts and visions for electronic and bioelectronic noses," Sens. Actuators B., 52, 1998, pp. 125-142.

Grate, J.W., "Acoustic Wave Microsensor Arrays for Vapor Sensing," Chem. Rev., 100, 2000, pp. 2627-2648.

Grate et al., "Sorptive Behavior of Monolayer-Protected Gold Nanoparticle Films: Implications for Chemical Vapor Sensing," Anal. Chem., 75, 2003, pp. 1868-1879.

Han et al., "Core-Shell Nanostructured Nanoparticle Films as Chemically Sensitive Interfaces," Anal. Chem., 73, 2001, pp. 4441-4449.

Han et al., "Nanoparticle-structured sensing array materials and pattern recognition for VOC detection," Sens. Actuators B, 106, 2005, pp. 431-441.

Harnack et al., "Lithographic patterning of nanoparticle films self-assembled from organic solutions by using a water-soluble mask," Appl. Phys. Lett., 86, 2005, 034108-034108-3.

Horinouchi et al., "Hydrogen Storage Properties of Isocyanide-Stabilized Palladium Nanoparticles,". Langmuir 2006, 22, 1880-1884.

Hostetler et al., "Dynamics of Place-Exchange Reactions on Monolayer-Protected Gold Cluster Molecules," Langmuir, 15, 1999, pp. 3782-3789.

Hostetler et al., "Stable, Monolayer-Protected Metal Alloy Clusters," J. Am. Chem. Soc., 120, 1998, pp. 9396-9397.

Huang et al., "Pd-Ni thin films grown on porous Al2O3 substrates by metalorganic chemical vapor deposition for hydrogen sensing," Thin Solid Films, 345, 1999, pp. 217-221.

Hughes et al., "Thin films of Pd/Ni alloys for detection of high hydrogen concentrations," J. Appl. Phys., 71, 1992, pp. 542-544.

Hughes et al., "Thin-film palladium and silver alloys and layers for metal-insulator-semiconductor sensors," J. Appl. Phys., 62, 1987, pp. 1074-1083.

Ibanez et al., "Ozone- and Thermally Activated Films of Palladium Monolayer-Protected Clusters for Chemiresistive Hydrogen Sensing," Langmuir, 22, 2006, pp. 9789-9796.

Ibanez et al., "Chemiresistive Vapor Sensing with Microscale Films of Gold Monolayer Protected Clusters," Anal. Chem., 78, 2006, pp. 753-761.

Isaacs et al., "Synthesis of Tetraoctylammonium-Protected Gold Nanoparticles with Improved Stability," Langmuir, 21, 2005, pp. 5689-5692.

Jana et al., "Wet Chemical Synthesis of High Aspect Ratio Cylindrical Gold Nanorods," J. Phys. B., 105, 2001, pp. 4065-4067.

Joseph et al., "Self-Assembled Gold Nanoparticle/Alkanedithiol films: Preparation, Electron Microscopy, XPS-Analysis, Charge Transport, and Vapor-Sensing Properties," Phys. Chem. B, 107, 2003, pp. 7406-7413.

Joseph et al., "Chemiresistor coatings from Pt- and Au-nanoparticle/ nanoedithiol films: sensitivity to gases and solvent vapors," Sens. Actuators B, 98, 2004, pp. 188-195.

Joseph et al., "Gold-nanoparticle/organic linker films: self-assembly, electronic and structural characterisation, composition and vapour sensitivity," Faraday Discuss., 125, 2004, pp. 77-97.

Kalli et al., "Characterization of reflectivity inversion, a- and b-phase transitions and nanostructure formation in hydrogen activated thin Pd films on silicon based substrates," Appl. Phys., 91, 2002, pp. 3829-3840.

Kalli et al., "Temperature-induced reflectivity changes and activation of hydrogen sensitive optically thin palladium films on silicon oxide," Rev. Sci. Instrum., 69, 1998, pp. 3331-3338.

Kallo et al., "Conductance and Methanol Crossover Investigation of Nation Membranes in a Vapor-Fed DMFC," J. Electrochem. Soc., 150, 2003, pp. 765-769.

Kaltenpoth et al., "Multimode Detection of Hydrogen Gas Using Palladium-Covered Silicon-Channels," Anal. Chem., 75, 2003, pp. 4756-4765.

Kang et al., "Comparison and analysis of Pd- and Pt-GaAs Schottky diodes for hydrogen detection," J. Appl. Phys., 75, 1994, pp. 8175-8181.

Kolmakov et al., "Enhanced Gas Sensing by Individual SnO Nanowires and Nanobelts Functionalized with Pd Catalyst Particles," Nano Lett., 5, 2005, pp. 667-673.

Kong et al., "Functionalized Carbon Nanotubes for Molecular Hydrogen Sensors," Adv. Mater., 13, 2001, pp. 1384-1386.

Krasteva et al., "Self-Assembled Gold Nanoparticle/Dendrimer Composite Films for Vapor Sensing Applications," Nano Lett., 2, 2002, pp. 551-555.

Krasteva et al., "Gold nanoparticle/PPI-dendrimer based chemiresistors Vapor-sensing properties as a function of the dendrimer size," Sens. Actuators B, 92, 2003, pp. 137-143.

Krasteva et al., "Vapor Sorption in Self-Assembled Nanoparticle/ Dendrimer Films Studied by Specular Neutron Reflectometry," Langmuir, 19, 2003, pp. 7754-7760.

Lavrik et al., "Cantilever transducers as a platform for chemical and biological sensors," Rev. of Sci. Inst., 75, 2004, pp. 2229-2253.

Leff et al., "Synthesis and Characterization of Hydrophobic, Organically,-Soluble Gold Nanocrystals Functionalized with Primary Amines," Langmuir, 12, 1996, pp. 4723-4730.

Leopold et al., "Growth, conductivity, and vapor response properties of metal ion-carboxylate linked nanoparticle films," Faraday Discuss., 125, 2004, pp. 63-76.

Lewis, N. S., "Comparisons between Mammalian and Artificial Olfaction Based on Arrays of Carbon Black-Polymer Composite Vapor Detectors," Acc. Chem. Res., 37, 2004, pp. 663-672.

Lin et al., "A Porous Silicon-Palladium Composite Film for Optical Interferometric Sensing of Hydrogen," Langmuir, 20, 2004, pp. 5104-5108.

Luo et al., "Thermal Activation of Molecularly-Wired Gold Nanoparticles on a Substrate as Catalyst," J. Am. Chem. Soc., 124, 2002, pp. 13988-13989.

Luo et al., "Spectroscopic Characterizations of Molecularly linked Gold Nanoparticle Assemblies upon Thermal Treatment," Langmuir, 20, 2004, pp. 4254-4260.

Luongo et al., "Development of a highly sensitive porous Si-based hydrogen sensor using Pd nano-structures," Sens. Actuators B, 111-112, 2005, pp. 125-129.

Lutz et al., "Hydrogen Sensing by Enzyme-Catalyzed Electrochemical Detection," Anal. Chem., 77, 2005, pp. 4969-4975.

Marubayashi et al., "Monolayer-Protected Au Cluster (MPC)-Supported Ti-BINOILate complex," Org. Lett, 5, 2003, pp. 4409-4412.

Mitsubayashi et al., "Gas-Phase Biosensor for Ethanol," Anal. Chem, 66, 1994, pp. 3297-3302.

Mizsei et al., "Structural transformations of ultra-thin sputtered Pd activator layers on glass and $SnO_2$ surfaces," Thin Solid Films, 391, 2001, pp. 209-215.

Morris et al., "Effects of hydrogen absorption on the electrical conduction of discontinuous palladium thin films," Int. J. Electronics, 81, 1996, pp. 441-447.

Niu et al., "Size-Selective Hydrogenation of Olefins by Dendrimer-Encapsulated Palladium Nanoparticles," J. Am. Chem. Soc., 123, 2001, pp. 6840-6846.

Norrod et al., "Ozone-Induced Oxidation of Self-Assembled Decanethiol: Contributing Mechanism for "Photooxidation"?," J. Am. Chem. Soc., 120, 1998, pp. 2656-2657.

Pang et al., "Humidity effect on the monolayer-protected gold nanoparticles coated chemiresistor sensor for VOCs analysis," Talanta, 65, 2005, pp. 1343-1348.

Pavlou et al., "Sniffing out the Truth: Clinical Diagnosis Using the Electronic Nose," Clin. Chem. Lab. Med., 38, 2000, pp. 99-112.

Poirier et al., "Molecular-Scale Characterization of the Reaction of Ozone with Decanethiol Monolayers on Au(111)," J. Am. Chem. Soc., 121, 1999, pp. 9703-9711.

Pundt A. et al., "Hydrogen and Pd-clusters," Mater. Sci. Eng., B108, 1004, pp. 19-23.

Qi et al., "Toward Large Arrays of multiplex Functionalized Carbon Nanotube Sensors for Highly Sensitive and Selective Molecular Detection," Nano Lett. 3, 2003, pp. 347-351.

Raber et al., "Technology Challenges in Responding to Biological or Chemical Attacks in the Civilian Sector," Science, 302, 1003, pp. 1350-1354.

Rakow et al., "A colorimetric-sensor array for odour visualization," Nature, 406, 2000, pp. 710-713.

Ramachandran et al., "An Overview of Industrial Uses of Hydrogen," Int. J. Hydrogen Energy, 23, 1998, pp. 593-598.

Rao et al., "Synthesis and characterization of lower size, laurylamine protected palladium nanoparticles," Materials Letters, 60, 1006, p. 3169.

Sachtler et al., "On the mechanism of catalytic hydrogenation of nitriles to amines over supported metal catalysts," Applied Catalysis A, 182, 1999, pp. 365-378.

Sakamoto et al., "Electrical resistance measurements as a function of composition of palladium-hydrogen (deuterium) systems by a gas phase method," Phys. : Condens. Matter, 8, 1996, pp. 3399-3411.

Santhanam et al., "Microcontact Printing of Uniform Nanoparticle Arrays," Nano Lett., 4, 2004, pp. 41-44.

Sayago et al., "Hydrogen sensors based on carbon nanotubes thin films," Synthetic Metals, 148, 2005, pp. 15-19.

Schalpbach et al., "Hydrogen-storage materials for mobile applications," Nature, 414, 2001, pp. 353-358.

Schoenfisch et al., "Air Stability of Alkanethiol Self-Assembled Monolayers on Silver and Gold Surfaces," J. Am. Chem. Soc. 120, 1998, pp. 4502-4513.

Senesac et al., "Analyte species and concentration identification using differentially functionalized microcantilever arrays and artificial neural networks," Analyt. Chim. Acta, 558, 2006, pp. 94-101.

Sheng et al., "Voltage-Induced Tunneling Conduction in Granular Metals at Low Temperatures," Phys. Rev. Lett., 28, 1972, pp. 34-37.

Shimizu et al., "Size Evolution of Alkanethiol-Protected Gold Nanoparticles by Heat Treatment in the Solid State," Phys. Chem. B, 107, 2003, pp. 2719-2724.

Sih et al., "Surface-plasmon resonance sensing of alcohol with electrodeposited polythiophene and gold nanoparticle-oligothiophene films," J. Appl. Phys., 98, 2005, pp. 114314-114314-4.

Smith et al., "Principles of quartz crystal microbalance/heat conduction calorimetry: Measurement of the sorption enthalpy of hydrogen in palladium," Thermochim. Acta, 432, 2005, pp. 202-211.

Snow et al., "Self-assembly of gold nanoclusters on micro- and nanoelectronic substrates," Mater. Chem., 12, 2002, pp. 1222-1230.

Su et al., "A Study of the dynamics of Pd Oxidation and PdO Reduction by $H_2$ and $CH_4$," Catal., 176, 1998, pp. 125-135.

Sun et al., "Ag Nanowires Coated wtih Ag/Pd Alloy Sheaths and Their Use as Substrates for Reversible Absorption and Desorption of Hydrogen," J. Am. Chem. Soc., 126, 2004, pp. 5940-5941.

Templeton et al., "Monolayer-Protected Cluster Molecules," Acc. Chem. Res., 33, 2000, pp. 27-36.

Terrill et al., "Monolayers in Three Dimensions: NMR, SAXS, Thermal, and Electron Hopping Studies of Alkanethiol Stabilized Gold Clusters," J. Am. Chem. Soc., 117, 1995, pp. 12537-12548.

Varghese et al., "Extreme Changes in the Electrical Resistance of Titania nanotubes with Hydrogen Exposure," Adv. Mater., 15, 2003, pp. 624-627.

Varghese et al., "Hydrogen sensing using titania nanotubes," Sens. Actuators B, 93, 2003, pp. 338-344.

Vossmeyer et al., "Gold Nanoparticle/Polyphenylene Dendrimer Composite films: Preparation and Vapor-Sensing Properties," Adv. Mater., 14, 2002, pp. 238-242.

Walter et al., "Palladium Mesowire Arrays for Fast Hydrogen Sensors and Hydrogen-Actuated Switches," Anal. Chem., 74, 2002, pp. 1546-1553.

Wang et al., "Array of Molecularly Mediated Thin Film Assemblies of Nanoparticles: Correlation of Vapor Sensing with Interparticle Spatial Properties," J. Am. Chem. Soc., 129, 2007, pp. 2161-2170.

Wohltjen et al., "Colloidal Metal-Insulator-Metal Ensemble Chemiresistor Sensor," Anal. Chem., 70, 1998, pp. 2856-2859.

Wolfe et al., "Fabrication of palladium-based microelectronic devices by microcontact printing," Appl. Phys. Lett., 80, 2002, pp. 2222-2224.

Wuelfing et al., "Electronic Conductivity of Solid-State, Mixed-Valent, Monolayer-Protected Au Clusters," J. Am. Chem. Soc., 122(46), 2000, pp. 11465-11472.

Yang et al., "Porous shape Persistent Fluorescent Polymer Films: An Approach to TNT Sensory Materials," J. Am. Chem. Soc., 120, 1998, pp. 5321-5322.

Yang et al., "Nerve Agents Detection Using a Cu/I-Cysteine Bilayer-Coated Microcantilever," J. Am. Chem. Soc., 125, 2003, pp. 1124-1125.

Yinon, J., "Detection of Explosives by Electronic Noses: Handheld chemical-sensing systems come in several varieties and offer advantages over the traditional bomb-sniffing dog," Anal. Chem., 2003, 99A-105A.

Yu et al., "Fabrication of Palladium Nanotubes and Their Application in Hydrogen Sensing," Chem. Mater., 17, 2005, pp. 3445-3450.

Yun et al., "Electrochemically Grown Wires for Individually Addressable Sensor Arrays," Nano Lett., 4, 2004, pp. 419-422.

Zamborini et al., "Synthesis, Characterization, Reactivity, and Electrochemistry of Palladium Monolayer Protected Clusters," Langmuir, 17, 2001, pp. 481-487.

Zamborini et al., A"Electron Hopping Conductivity and Vapor Sensing Properties of Flexible Network Polymer Films of Metal Nanoparticles," Am. Chem. Soc., 124, 2002, pp. 8958-8964.

Zamborini et al., "Distance-dependent electron hopping conductivity and nanoscale lithograpy of chemically-linked gold monolayer protected cluster films," Anal. Chim. Acta, 496, 2003, pp. 3-16.

Zhang et al., "Ozonolysis Is the Primary Cause of UV Photooxidation of Alkanethiolate Monolayers at Low Irradiance," J. Am. Chem. Soc., 120, 1998, pp. 2654-2655.

Zhang et al., "Ultraviolet Photochemistry and ex Situ Ozonolysis of Alkanethiol Self-Assembled Monolayers on Gold," Chem. Mater., 11, 1999, pp. 2191-2198.

Zhao et al., "Annealing enhanced hydrogen absorption in nanocrystalline Pd/Au sensing film," J. Appl. Phys., 97, 2005, pp. 124301-124301-7.

Zhao et al., "All-Optical Hydrogen-Sensing Materials Based on Tailored Palladium Alloy thin Films," Anal. Chem., 76, 2004, pp. 6321-6326.

Zhao et al., "All-optical hydrogen sensor based on a high alloy content palladium thin film," Sens Actuators B 2006, 113, 532-538.

Ancona et al., "Scaling Properties of Gold Nanocluster Chemiresistor Sensors," IEEE Sensors Journal, 6, 2006, pp. 1403-1414.

ISA/US, International Search Report and Written Opinion for international application No. PCT/US08/71276, mailed Oct. 2, 2008.

* cited by examiner

CHEMICAL SENSORS FOR DETECTING HYDROGEN AND METHODS OF USE

RELATED APPLICATIONS

The presently-disclosed subject matter claims the benefit of U.S. Provisional Patent Application Ser. No. 60/952,125, filed Jul. 26, 2007; the disclosure of which is incorporated herein by reference in its entirety.

GOVERNMENT INTEREST

Subject matter described herein was made with U.S. Government support under Grant Number CHE0518561 awarded by the National Science Foundation. The government has certain rights in the described subject matter.

TECHNICAL FIELD

The presently-disclosed subject matter relates to sensors and methods for detecting hydrogen. In particular, the presently-disclosed subject matter relates to sensors and methods for detecting hydrogen wherein the conductivity of a chemiresistant film is increased upon exposure to hydrogen.

INTRODUCTION AND GENERAL CONSIDERATIONS

Hydrogen ($H_2$) is a useful energy source that has the potential to reduce the need for fossil-fuels in the future, and may someday replace or serve as an important alternative to the current fossil-based transportation fuels. A great deal of effort has been put forth to develop hydrogen-fueled motor vehicles in order to fulfill increasing energy demands for transportation. Also, hydrogen is present as a common reagent in industry and is used as an $O_2$ scavenger in metallurgy, in hydrocracking for refined fuels, and in degradation of synthetic materials [1]. However, utilizing $H_2$ can be dangerous, as $H_2$ has one of the lowest flash points (−253° C.) of any energy source making it highly explosive in air above 4% by volume [2]. Accordingly, one of the aims in fuel cell research is to safely store and release $H_2$ in a controlled manner [3,4,5]. For these reasons, it is important to develop simple, reliable, low cost sensors for the detection of $H_2$ over a range of concentrations.

Early chemiresistive $H_2$ sensors were based on conductive palladium (Pd) films whose resistance increased in the presence of hydrogen due to the formation of the more resistive PdHx [6,7]. More recent reports on this type of sensing mechanism demonstrated improved response times, higher sensitivity, and lower detection limits by using nanostructured materials (e.g., Pd nanotubes) [8]. Another type of sensing mechanism involved the use of Pd nanowires [9,10] or films of nanoparticles [11,12] that contain disconnected, high resistance metal-metal junctions. These materials exhibit a decrease in resistance in the presence of $H_2$ due to the formation of PdHx, which expands in volume and forms a more connected, lower resistance structure. This behavior was demonstrated with Pd mesowires electrochemically synthesized by step-edge decoration of highly-oriented pyrolytic graphite (HOPG) [9,10,13] and lithographically fabricated Pd wires [14,15]. Similar behavior has been described for discontinuous films of Pd, which contain Pd nanoparticles evaporated or sputtered so that they are below the percolation threshold for conductivity [11,12,16,17]. The importance of the functionality of the substrate that the Pd is deposited on has also been demonstrated [12]. In general, these types of sensors exhibit very fast, reversible, and sensitive responses with detection limits as low as 0.05 ppm and response times on the order of ms [9,12].

The reactivity of alkanethiolate-coated Pd monolayer-protected clusters (MPCs) to hydrogen for chemiresistive sensing applications is also appreciated [18]. The use of films of chemically-synthesized Pd nanoparticles for $H_2$ sensing had several benefits over evaporated or sputtered Pd films in terms of simplicity, cost, reproducibility, and control over the electronic properties and sensing behavior. Yet, while the electronic properties of those alkanethiolate-coated Pd MPCs could be tailored by the surrounding monolayer, the presence of the strongly chemisorbed thiolate group prevented the reaction between Pd and $H_2$. Thus, ozone or heat treatment was required to desorb thiolates from the surface and promote $H_2$ reactivity, which is inconvenient and more complicated.

Accordingly, there remains a need in the art for sensors and methods for detecting hydrogen. In particular, there is an unmet need for sensors and methods for detecting hydrogen whereby nanoparticles are deposited as a film on a sensor and directly utilized for $H_2$ sensing without first treating the nanoparticles with ozone or heat.

SUMMARY

This Summary lists several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter, a sensor for detecting hydrogen is provided. The sensor comprises, in some embodiments, an electrically insulating support; at least two electrodes positioned at a distance from one another and affixed to the support; and, a chemiresistant film deposited at least between the electrodes and comprising alkylamine-coated metal alloy nanoparticles, wherein conductivity of the chemiresistant film is increased upon exposure to hydrogen.

In some embodiments, the sensor comprises an alkylamine that is a compound of Formula (I): $CH_3(CR_1R_2)_n(NR_3R_4)$—, where n is an integer from 3 to 15 and $R_1$, $R_2$, $R_3$, and $R_4$ are each independently selected from the group consisting of H, alkyl, and substituted alkyl. In some embodiments, the alkylamine is selected from the group consisting of $C_6H_{13}NH_2$—, $C_8H_{17}NH_2$—, and $C_{12}H_{25}NH_2$—

The presently-disclosed subject matter further provides, in some embodiments, a sensor for detecting hydrogen wherein the chemiresistant film further comprises alkylthiolate-coated metal alloy nanoparticles. In some embodiments, the alkylthiolate is a compound of Formula (II): $CH_3(CR_1R_2)_nS$—, where n is an integer from 3 to 15 and $R_1$ and $R_2$ are each independently selected from the group consisting of H, alkyl, and substituted alkyl. In some embodiments, the alkythiolate is $C_6H_{13}S$—.

In some embodiments, a sensor is provided where the chemiresistant film comprises surfactant-coated metal alloy nanoparticles, wherein the surfactant is a compound of Formula (III): $[CH_3(CR_1R_2)_n]_4NR_3$; where n is an integer from 3 to 15; $R_1$ and $R_2$ are each independently selected from the group consisting of H, alkyl, or substituted alkyl; and, $R_3$ is selected from the group consisting of $Cl^-$, $I^-$, $NO_3^-$, $SO_4^{2-}$, $ClO_4^{2-}$, and $PF_6^-$. In some embodiments, the surfactant is tetraoctylammonium bromide (TOABr).

In some embodiments of the sensors of the presently-disclosed subject matter, the chemiresistant film is drop-cast deposited at least between the at least two electrodes. In some embodiments, the chemiresistant film is micro-contact printed at least between the at least two electrodes.

In some embodiments of the presently-disclosed subject matter, a sensor is provided wherein the support and the electrodes are inert to hydrogen. In some embodiments, the distance between the electrodes is about 100 nanometers to about 1 millimeter. In some embodiments, the distance between the electrodes is about 23 micrometers. Further, in some embodiments, the conductivity is reversible.

In some embodiments of the sensors of the presently-disclosed subject matter, the metal alloy is selected from the group consisting of a palladium alloy, a palladium/gold alloy, and a palladium/silver alloy.

The presently-disclosed subject matter further provides, in some embodiments, a method for detecting hydrogen in a sample. In some embodiments, the method comprises providing a sensor according to the presently-disclosed subject matter, applying a voltage potential between at least two electrodes, exposing the sensor to a gas sample, and, detecting a change in the current between the at least two electrodes to thereby detect hydrogen in the sample. In some embodiments of the methods of the presently-disclosed subject matter, the hydrogen is present in the gas sample at a concentration of at least about 0.08%. In some embodiments, the hydrogen is present in the gas sample at a concentration of about 9.6% to about 0.08%.

Accordingly, it is an object of the presently-disclosed subject matter to provide sensors and methods for detecting hydrogen. This object is achieved in whole or in part by the presently-disclosed subject matter.

An object of the presently-disclosed subject matter having been stated hereinabove, and which is achieved in whole or in part by the presently-disclosed subject matter, other objects and advantages will become evident to those of ordinary skill in the art after a study of the following description of the presently-disclosed subject matter, Figures, and non-limiting Examples.

BRIEF DESCRIPTION OF THE FIGURES

FIG. 2A includes CVs of drop-cast deposited films of $C_8H_{17}NH_2$—(C8 $NH_2$ Pd), $C_{12}H_{25}NH_2$—(C12 $NH_2$ Pd), and $C_{16-18}H_{33-36}NH_2$-coated Pd nanoparticles (C16-18 $NH_2$ Pd), and TOABr-coated Pd nanoparticles (TOABr Pd) obtained in air from +0.3 V to −0.3 V (started at 0.0 V) at a sweep rate of 100 mV/s. FIG. 2B includes expanded CVs of films of $C_{12}H_{25}NH_2$-coated Pd and $C_{16-18}H_{33-36}NH_2$-coated Pd nanoparticles as indicated by the dashed rectangle in FIG. 2A. FIG. 2C includes chronoamperometry (CA) plots of the same drop-cast films from FIG. 2A measured in air at −0.3 V for 1000 s.

FIGS. 8E and 8F show the same film after an additional 1 h exposure to air. Circles labelled #1 represent areas of where the film changed significantly after 1 h exposure to air and circles labelled #2 represent areas were the film remained very similar.

DETAILED DESCRIPTION

Figure 1:
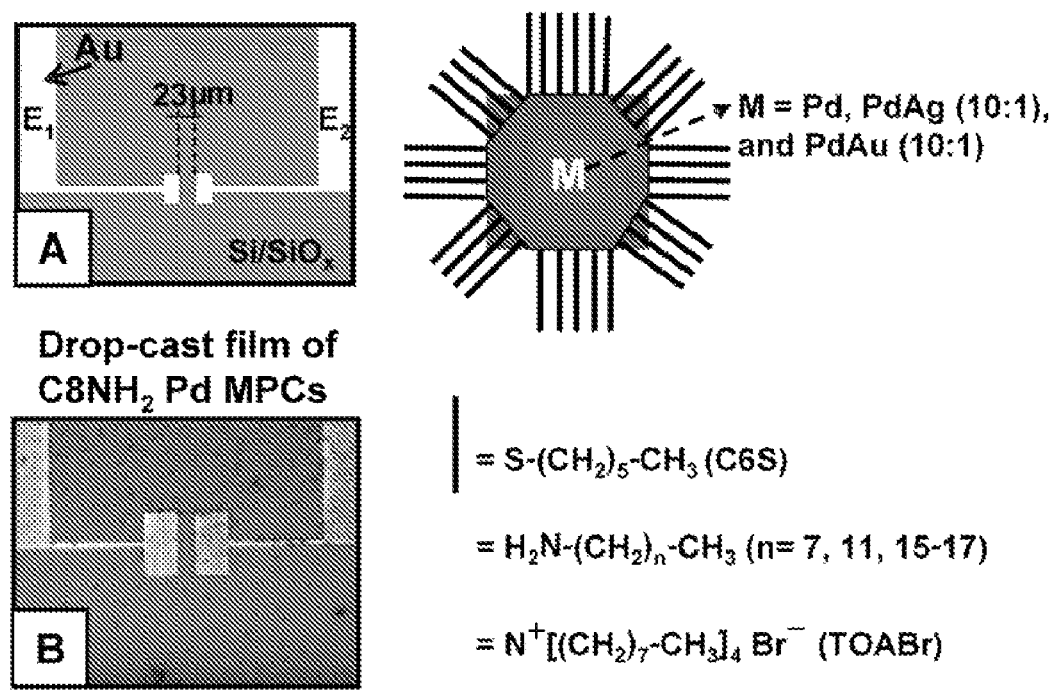
FIG. 1 includes optical microscope images of an exemplary sensor before (A) and after (B) drop-cast deposition of a film of $C_8H_{17}NH_2$-coated Pd nanoparticles (C8 $NH_2$ Pd MPCs) between a 23 μm electrode gap. The scheme of the nanoparticle shows different exemplary metal compositions and different exemplary ligand stabilizers.

The details of one or more embodiments of the presently-disclosed subject matter are set forth in the accompanying description below. Other features, objects, and advantages of the presently-disclosed subject matter will be apparent from the specification, Figures, and Claims. All publications, patent applications, patents, and other references noted herein are incorporated by reference in their entirety. In case of conflict, the present specification, including definitions, will control.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods and materials are now described.

Following long-standing patent law convention, the terms "a", "an", and "the" refer to "one or more" when used in this application, including the claims. Thus, for example, reference to "a sensor" includes a plurality of such sensors, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

The presently-disclosed subject matter includes sensors and methods of using same for detecting hydrogen. Hydrogen (H$_2$) is thought to be a feasible source of energy that can replace or serve as an important alternative to the current fossil-based transportation fuels. Also, H$_2$ is present as a common reagent in industry and is used as an oxygen (O$_2$) scavenger in metallurgy, in hydrocracking for refined fuels, and in degradation of synthetic materials. However, H$_2$ has one of the lowest flash points of any source (−253° C.) making it highly explosive above 4% by volume. As such, applications for H$_2$ require sensors that can detect flow and leakage at early stages.

Thus, in some embodiments of the presently-disclosed subject matter, a sensor for detecting H$_2$ over a range of concentrations is provided that can be used in a variety of applications, including, but not limited to, H$_2$ fuel sources for transportation. The terms "detect," "detecting," and grammatical variations thereof, are used herein to refer to determining the presence or absence and measuring the amount of H$_2$. As such, "detecting" H$_2$ can refer to a determination of whether hydrogen is present or absent in a sample of interest as well as quantifying the amount of hydrogen that is present in a sample of interest. For example, to quantify the amount of hydrogen present in a sample a calibration curve is obtained by measuring the response of a sensor, or the analytical signal, to known hydrogen concentrations, i.e. standards. The analytical signal used for the detection of H$_2$ is the percent response as described by the following equation:

$$\% \text{ Response} = (i_r - i_b)/i_b * 100\%$$

where $i_b$ is the initial sensor baseline current in the presence of 100% N$_2$ and $i_r$ is the sensor current in the presence of a H$_2$/N$_2$ mixture of a certain standard percent H$_2$. A negative value is equal to a decrease in the current upon exposure to H$_2$ and vice-versa. The calibration curve is a plot of H$_2$ concentration (x-axis) versus % response (y-axis). From this curve, the concentration of H$_2$ in unknown samples can thus be determined.

In some embodiments of the presently-disclosed subject matter, the sensor for detecting hydrogen comprises an electrically insulating support; at least two electrodes positioned at a distance from one another and affixed to the support; and, a chemiresistant film deposited at least between the electrodes and comprising alkylamine-coated metal alloy nanoparticles, wherein the conductivity of the chemiresistant film is increased upon exposure to hydrogen.

As used herein, the phrase "electrically insulating support" refers to a substrate that resists the flow of electrical current and can be used to support or separate electrical conductors while providing low background conductivity or without allowing current to travel via the support itself. For example, an "electrically insulating support" can include, but is not limited to, substrates comprised of glass, porcelain, composite materials, polymers such as plastics, silicates such as mica, silicon nitride, ceramics, and silicon oxide. In some embodiments, the support and the electrodes are inert to hydrogen gas.

The electrodes of the presently-disclosed sensors can be comprised of any electrically conductive material through which an electric current may enter and leave. Such electrodes are known to those of ordinary skill in the art and include, but are not limited to, silver and gold electrodes that can be affixed to a support. The term "affixed" is used herein to refer to the attachment of electrodes to a support. For example, silver electrodes may be affixed to glass by painting the silver electrodes onto a glass support with a clean pipette or sharp metal tip, such as a glass chromatography syringe. As another example, gold electrodes may be fabricated by photolithography and affixed to a silicon support by sputtering and depositing gold over a suitable adhesion layer such as a chromium adhesion layer.

An exemplary sensor of the presently disclosed subject matter typically comprises at least two electrodes. The phrase "at least two electrodes" is used herein to refer to two or more electrodes that are positioned at a distance from one another such that the current running between the two electrodes can be measured. In some embodiments, the distance between the electrodes is about 100 nanometers to about 1 millimeter. In some embodiments, the distance between the electrodes is about 23 micrometers.

A criterion regarding the distance between the at least two electrodes is that the films conduct electricity across the gap between the at least two electrodes. As such, the upper limit of the distance between the at least two electrodes can be set by the appearance of possible discontinuities or breaks in the film that would prevent conductivity. For example, distances of approximately 100 nm can be used for micro-contact printed chemiresistant films as the micro-contact printed chemiresistant films are generally continuous and conductive over this distance, but can have discontinuities over longer distances that prevent conductivity. As another example, drop-cast chemiresistant films are generally continuous over distances from about 100 nm to about 1 mm or more, so conductivity is possible over longer distances.

The phrase "chemiresistant film," as used herein, refers to films of materials whose conductivity changes in the presence of a vapor or gas analyte. Typically, when a vapor or gas analyte partitions into such a film, the vapors or gas analytes diffuse and absorb onto the materials which comprise the film and the resulting change in conductivity is proportional to the amount of vapor absorbed into the film. As such, in some embodiments of the sensors of the presently-disclosed subject matter, the chemiresistant film deposited at least between the electrodes is comprised of alkylamine-coated metal alloy nanoparticles. The term "alkylamine" is used herein to refer to an alkyl group that is bonded to an amino group. The term "amino" refers to an $-NR_3R_4$ group where $R_3$ and $R_4$ are each independently selected from the group consisting of H, alkyl, and substituted alkyl.

As used herein the term "alkyl" refers to $C_{4-16}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 4 to about 8 carbon atoms (i.e., a $C_{4-8}$ alkyl), e.g., 4, 5, 6, 7, or 8 carbon atoms. "Higher alkyl" refers to an alkyl group having about 10 to about 16 carbon atoms, e.g., 10, 11, 12, 13, 14, 15, or 16 carbon atoms. In certain embodiments, "alkyl" refers, in particular, to $C_{4-16}$ straight-chain alkyls. In other embodiments, "alkyl" refers, in particular, to $C_{4-16}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen or alkyl.

Thus, as used herein, the term "substituted alkyl" includes alkyl groups, as defined herein, in which one or more atoms or functional groups of the alkyl group are replaced with another atom or functional group, including, for example, alkyl, substituted alkyl, halogen, aryl, substituted aryl, alkoxyl, hydroxyl, nitro, amino, alkylamino, dialkylamino, sulfate, and mercapto.

Further, as used herein, the terms alkyl and/or "substituted alkyl" include an "allyl" or an "allylic group." The terms "allylic group" or "allyl" refer to the group $-CH_2HC=CH_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

In some embodiments, the alkylamine is a compound of Formula (I):

$$CH_3(CR_1R_2)_n(NR_3R_4)- \qquad (I)$$

where n is an integer from 3 to 15 and $R_1$, $R_2$, $R_3$, and $R_4$ are each independently selected from the group consisting of H, alkyl, and substituted alkyl. Further, in some embodiments, the alkylamine is selected from the group consisting of $C_6H_{13}NH_2-$, $C_8H_{17}NH_2-$, and $C_{12}H_{25}NH_2-$.

The presently-disclosed subject matter further provides, in some embodiments, a sensor for detecting hydrogen wherein the chemiresistant film further comprises alkylhiolate-coated metal alloy nanoparticles. In this regard, the metal alloy nanoparticles of the presently-disclosed subject matter can be coated with a mixed monolayer comprised of alkylamine and alkylthiolate groups such that a single metal alloy nanoparticle contains both alkylamine groups and alkylthiolate groups. The term "thiol" refers to a sulfur containing $-SH$ group. As such, the term "thiolate" is used herein to refer to a deprotonated thiol group, or $-S^-$. In some embodiments, the alkylthiolate is a compound of Formula II:

$$CH_3(CR_1R_2)_nS- \qquad (II)$$

where n is an integer from 3 to 15 and $R_1$ and $R_2$ are each independently selected from the group consisting of H, alkyl, and substituted alkyl. In some embodiments, the alkylhiolate is $C_6H_{13}S-$.

In some embodiments of the presently-disclosed subject matter, a sensor is provided wherein the chemiresistant film comprises surfactant-coated metal alloy nanoparticles, wherein the surfactant is a compound of Formula (III):

$$[CH_3(CR_1R_2)_n]_4NR_3 \qquad (III)$$

where n is an integer from 3 to 15; $R_1$ and $R_2$ are each independently selected from the group consisting of H, alkyl, or substituted alkyl; and, $R_3$ is selected from the group consisting of $Cl^-$, $I^-$, $NO_3^-$, $SO_4^{2-}$, $ClO_4^{2-}$, and $PF_6^-$. In some embodiments, the surfactant is tetraoctylammonium bromide (TOABr).

The term "metal alloy nanoparticles" is used herein to refer to nanoparticles comprised of at least two elements, one of which is a metal. The term "nanoparticles" includes particles having an average size of, in some embodiments, between about 2 and about 100 nm, in some embodiments, between about 2 and about 50 nm and, in some embodiments, between about 2 and about 10 nm. A metal alloy of the presently-disclosed subject matter can be comprised of a pure metal alloy or mixtures of metal alloys. For example, the metal alloy can be a core/shell particle that contains one metal in the core and another metal as a surrounding shell. As another example, the metal alloy can be a mixed alloy that is an even mixture of two metals throughout the particle. As yet another example, the metal alloy can be a phase-segregated alloy, where the metal alloy has different separate phases of each metal in the nanoparticle, but are not necessarily arranged as a core and shell.

In accordance with the presently-disclosed subject matter the metal alloy nanoparticles can comprise a roughly spherical metal core that is surrounded by an organic monolayer, which, in some embodiments, can comprise an alkylamine, an alkylthiolate, or a surfactant. In this regard, the term "metal alloy nanoparticles" can be used interchangeably with the phrase "monolayer protected clusters" or "MPCs." In some embodiments, the roughly spherical metal core can have a diameter of about 1 to about 3 nanometers and the roughly spherical metal core surrounded by an organic monolayer can have a diameter of about 2 to about 5 nanometers. [42] Further, the metal alloy nanoparticles surrounded by an organic monolayer can be taken from a solution in which they are soluble and then deposited as films between electrodes where conductivity of the film is then increased upon exposure to hydrogen.

In some embodiments of the presently-disclosed subject matter, the metal alloy comprises palladium and a metal selected from the group consisting of gold, silver, and combinations thereof. In some embodiments, the metal alloy is selected from the group consisting of a palladium alloy, a palladium/gold alloy, and a palladium/silver alloy. The reaction between hydrogen and Pd or Pd-containing alloys is of great interest because of its relevance in hydrogen sensing and heterogeneous and homogeneous catalysis. It is appreciated that hydrogen spontaneously adsorbs to Pd as atomic hydrogen and diffuses into the lattice to form PdHx [6]. The initial α-phase Pd becomes β-phase PdHx through an α-β phase transition. The Pd lattice spacing changes throughout these phase changes, depending on the hydrogen concentration in the surrounding atmosphere [2,6]. The phase transitions and changes in lattice spacing lead to measurable changes in the optical properties [19-27], resistance [7-14, 16-17, 28-38] and mass [2,24] of the Pd.

Without wishing to be bound by theory, it is believed that upon exposure to $H_2$, PdHx forms and the chemiresistant films restructure and expand in volume to create more connected structure with fewer high resistance structures, thus lowering the resistance between the electrodes and increasing conductivity of the chemiresistant film upon exposure to $H_2$. Further, the conductivity of the chemiresistant films decreases with decreasing concentrations of $H_2$. As such, in some embodiments, the conductivity is reversible.

Typically, to exhibit reversible $H_2$ sensing behavior, films of alkylamine-coated Pd nanoparticle are first conditioned with 100% $H_2$. Upon the first exposure to 100% $H_2$ during the conditioning, the conductivity of films of alkylamine-coated Pd nanoparticles increases irreversibly by 1 to 5 orders of magnitude, depending on the metal used (Pd, Pd/Ag, or Pd/Au) and alkyl chain length (e.g., $C_4$-$C_{16}$). This large increase in current can be attributed to an irreversible morphological restructuring of the Pd in the film due to the incorporation of atomic H into the Pd lattice, forming $PdH_x$, which increases the size of the nanoparticles and causes direct irreversible contact between the Pd nanoparticles. Removal from the hydrogen environment causes hydrogen to be removed from the film, but the film has been irreversibly altered due to the connections made between the Pd nanoparticles. Subsequent exposures to and removal of hydrogen after conditioning exhibit a reversible increase or decrease in current. The response direction (increase or decrease) depends on the metal composition (Pd, Pd/Ag, or Pd/Au) and the alkyl chain length (e.g., $C_4$-$C_{16}$). An increase in current occurs for films that are still highly resistive after conditioning due to more connections made in the film upon the volume expansion of $PdH_x$ versus Pd. A decrease in current occurs for films that have a low resistance after conditioning due to an even larger resistance for $PdH_x$ compared to Pd. There is a competition between the increase in resistance associated with $PdH_x$ versus Pd and the decrease in resistance associated with volume expansion of $PdH_x$ versus Pd. One mechanism depends on the initial resistance of the film. The conditioning step and two sensing mechanisms apply specifically to films of alkylamine-coated Pd MPCs. TOABr coated Pd nanoparticles do not exhibit an irreversible conditioning step.

In some embodiments, the chemiresistant films of the presently-disclosed subject matter are deposited at least between the two electrodes of the sensors. As used herein, the phrase "at least between" is used to refer to the location where the chemiresistant films are deposited onto the support. For example, the chemiresistant films can be deposited onto the support such that the film is present only in the space between the electrodes. As another example, the chemiresistant films can be deposited on the support such that the film is present in the space between the electrodes and over the electrodes. Further, as another example, the chemiresistant film can be deposited on the support such that the film is present on a substantial portion of the support including, but not limited to, the space between the electrodes, over the electrodes, and over other areas of the support.

In some embodiments of the sensors of the presently-disclosed subject matter, the chemiresistant film is drop-cast deposited at least between the at least two electrodes. In this regard, one or more drops of a solution in which alkylamine-, alkylthiolate-, and/or surfactant-coated metal alloy nanoparticles are solubilized, e.g. with toluene, can be deposited drop wise at least between the two electrodes and allowed to dry until the solvent has evaporated.

In some embodiments of the sensors of the presently-disclosed subject matter, the chemiresistant film is micro-contact printed at least between the two electrodes. In this regard, a solution comprising coated nanoparticles can be used as ink for micro-contact printing onto solid substrates [39]. Methods of micro-contact printing include inking a patterned polydimethylsiloxane (PDMS) stamp with featured lines (e.g. lines approximately 1.3 μm wide, approximately 0.5 μm long, with approximately 2.2. μm separation) with a chemiresistant film solution, allowing the solution to dry for several minutes, and then bringing the stamp into contact with a support for several seconds.

Further provided, in some embodiments of the presently-disclosed subject matter, is a method for detecting hydrogen in a sample. In some embodiments, the method comprises providing a sensor in accordance with the presently disclosed subject matter; applying a voltage potential between at least two electrodes; exposing the sensor to a gas sample; and detecting a change in the current between the at least two electrodes to thereby detect hydrogen in the sample. In some embodiments of the method, the hydrogen is present in the gas sample at a concentration of at least about 0.08%. In some embodiments, the hydrogen is present in the gas sample at a concentration of about 9.6% to about 0.08%.

EXAMPLES

The following Examples have been included to illustrate modes of the presently-disclosed subject matter. In light of the present disclosure and the general level of skill in the art, those of skill will appreciate that the following Examples are intended to be exemplary only and that numerous changes, modifications, and alterations can be employed without departing from the scope of the presently-disclosed subject matter.

Materials and Methods for Examples 1-9

Chemicals

The following chemicals were used as received. Sodium borohydride (99%), tetraoctylammonium bromide (99%), toluene (99.9%), and 2-propanol (99.9%), were purchased from VWR Scientific Products. Octylamine ($C_8H_{17}NH_2$) and dodecylamine ($C_{12}H_{25}NH_2$) were purchased from Aldrich Chemical Co. 1-hexadecylamine ($C_{16}H_{36}NH_2$) containing $C_{18}H_{37}NH_2$ and 1-octadecylamine ($C_{18}H_{37}NH_2$) were purchased from Alfa Aesar Co. Barnstead Nanopure water (17.8 MΩ-cm) was employed for all aqueous solutions.

Synthesis of Hexanethiolate-Coated Pd Nanoparticles

Hexanethiolate-coated ($C_6H_{13}S$—) Pd nanoparticles were synthesized according to a modified Brust reaction [40-42]. Briefly, 0.40 g of $K_2PdCl_4$ was dissolved in 25 ml of water and 1.00 g of tetraoctylammonium bromide (TOABr) was dissolved in 150 ml of toluene. The two solutions were combined and stirred until all of the $PdCl_4^{2-}$ transferred into the toluene phase. The toluene phase was separated and 90 µl of hexanethiol, corresponding to a 1:2 thiol:Pd ratio, was added to the toluene and stirred. The solution was cooled to approximately 0° C. using an ice bath and a 10-fold excess of $NaBH_4$ (0.46 g in 10 ml of water) with respect to Pd was added to the toluene solution with stirring. The solution turned black within a few seconds, indicating the formation of metallic Pd MPCs. 10 ml of additional water was added and the solution was stirred overnight. The toluene layer was separated and removed by rotary evaporation. The remaining black solid was suspended in 200 ml of acetonitrile and collected by filtration on a glass fritted Büchner funnel. The black solid product was washed with an additional 250 ml of acetonitrile and thoroughly dried before collecting. The average diameter of hexanethiolate-coated Pd nanoparticle prepared this way is approximately 3.0 nm [42].

Synthesis of Alkylamine-Coated Pd, Pd/Ag, and Pd/Au Nanoparticles

Alkylamine-coated Pd nanoparticles were synthesized similar to hexanethiolate-coated Pd nanoparticles and alkylamine-coated Au nanoparticles [43]. Briefly, 0.50 g (1.59 mmol) of $K_2PdCl_4$ was dissolved in 20 ml of water and 1.92 g (3.51 mmol) of tetraoctylammonium bromide (TOABr) was dissolved in 100 ml of toluene by ultrasonication for 10 min. The two solutions were combined and stirred until all of the $PdCl_4^{2-}$ transferred into the toluene phase. The appropriate alkylamine ligand was then added to the rapidly stirring mixture in a 12:1 alkylamine:Pd ratio and allowed to stir for an additional 2 h. This ratio corresponds to 0.019 mol of alkylamine, which is 3.10 ml for octylamine ($C_8H_{17}NH_2$), 3.39 g for dodecylamine ($C_{12}H_{25}NH_2$), and 4.42 g for 1-hexadecylamine containing 1-octadecylamine ($C_{16}H_{36}NH_2/C_{18}H_{37}NH_2$). The aqueous layer immediately turned a beige/murky white upon addition of the alkylamine presumably due to the formation of a complex between the protonated amine and the $PdCl_4^{2-}$. After approximately 2 hours of stirring, 0.84 g $NaBH_4$ (0.022 mol) was dissolved in 10 ml of water and added to the two-phase solution with stirring. The solution turned black within a few seconds, indicating the formation of coated-Pd nanoparticles. 10 ml of additional water was added and the solution stirred overnight. The white and cloudy precipitate in the water phase disappeared and became colorless as the reaction proceeded. The toluene layer was separated and removed by rotary evaporation. The remaining black solid was suspended in 200 ml of acetonitrile and collected by filtration on a glass fritted Büchner funnel. The black solid product was washed with an additional 150 ml of acetonitrile, 150 ml of ethanol, and thoroughly dried before collecting. The average diameter of $C_8H_{17}NH_2$-coated Pd nanoparticles was 3.0±0.8 nm as determined by atomic force microscopy (AFM) measurements.

Alkylamine-coated Pd/Ag and Pd/Au alloy nanoparticles were synthesized in a 10:1 Pd:Ag or Pd:Au ratio by adding the corresponding salts in a 10:1 ratio in the reaction mixture. $AgC_2F_3O_2$ and $HAuCl_4 \cdot 3H_2O$ were used for Ag and Au, respectively. $AgC_2F_3O_2$ was directly soluble in the toluene phase while $AuCl_4^-$ was phase transferred into toluene with TOABr along with $PdCl_4^{2-}$. The amount of alkylamine and $NaBH_4$ was 12:1 and 15:1 with respect to total metal content. Nuclear magnetic resonance (NMR) and UV-vis spectroscopy measurements on coated Pd, Pd/Ag, and Pd/Au nanoparticles was consistent with the successful synthesis of coated Pd, Pd/Ag, and Pd/Au nanoparticles.

Synthesis of TOABr-Coated Pd and Pd/Ag Nanoparticles

Tetraoctylammonium bromide (TOABr)-coated Pd nanoparticles were synthesized in a manner similar to the hexanethiolate coated Pd nanoparticles, except the hexanethiol was not added. TOABr-stabilized nanoparticles are insoluble when isolated as a powder [44]. Thus, after reduction and separation from the water phase, the toluene solution containing the particles was reduced to approximately 50 ml by rotary evaporation, filtered with a microdisc filter (acrodisc, 2 µm PTFE membrane) to remove insoluble materials, and then used from solution. TOABr-coated Pd/Ag alloy nanoparticles were synthesized by adding $AgC_2F_3O_2$ to the solution in a final 10:1 Pd:Ag molar ratio and performing the rest of the synthesis the same as that for pure Pd. The 10-fold excess of $NaBH_4$ was with respect to the total metal. The average diameter of TOABr-coated Pd nanoparticles was 7.0±0.5 nm as determined by AFM measurements. UV-vis spectroscopy was consistent with the formation of metal nanoparticles, but NMR was not possible since the product could not be purified and isolated as a solid.

Sensor Device

Two Au electrodes separated by 23 µm were fabricated in a clean room by photolithography on a $Si/SiO_x$ substrate. The 100 nm thick Au electrodes were sputtered over a 10 Å thick Cr adhesion layer during the process. Wire leads were attached to the Au electrodes with Ag epoxy (cured 12 h, 80° C.) which was further insulated with an overlayer of torr-seal epoxy (cured 12 h, 80° C.). The electrode was cleaned by rinsing in acetonitrile, dichloromethane, acetone, ethanol, and 2-propanol before drying under $N_2$. The device was then placed in a UVO ozone cleaner (Jelight Company Inc., Irvine, Calif.) for 10 min before depositing the films of nanoparticles over the electrodes. Films of alkylamine-coated nanoparticles were drop-cast deposited using 1 to 3 drops of a 4 to 70 mg/ml toluene solution. The concentration and number of drops were chosen to obtain current through the film above the baseline. Films of TOABr-coated nanoparticles were drop-cast deposited using 2 drops of an approximately 2.6 mg/ml toluene solution, which is the concentration in terms of Pd when reducing the volume to 50 ml by rotary evaporation.

Gas Sensing

Gas sensing was performed with a CH Instruments 660A (Austin, Tex.) electrochemical workstation operating in chronoamperometry mode. The current was monitored with time while a −0.3 V potential was applied between the two electrodes and the sample was exposed to alternating flows of pure $N_2$ or air and different concentrations of $H_2$ in the $N_2$ or air carrier gas. A range of $H_2$ concentrations was obtained using a set of flow meters (Cole Parmer, 2% error at full scale) located between the sample and gas cylinders and operated by a 3-way valve, which allows a constant $H_2$ flow during mixing with $N_2$ and avoids over-pressures and artificial current spikes during sensing. The different concentrations of $H_2$ and the total flow rates ($H_2+N_2$/air) used were as follows: 9.6±0.3% (3.1±0.1 L.min$^{-1}$), 6.2±0.2% (4.9±0.1 L.min$^{-1}$), 3.2±0.1% (4.7±0.1 L.min$^{-1}$), 1.0±0.1% (4.7±0.1 L.min$^{-1}$), 0.50±0.02% (4.6±0.1 L.min$^{-1}$), 0.21±0.02% (4.6±0.1 L.min$^{-1}$), 0.11±0.02% (4.6±0.1 L.min$^{-1}$), 0.08±0.02% (4.6±0.1 L.min$^{-1}$). The flow rates and $H_2$ concentrations were similar using $N_2$ or air as the carrier gas due to their similar density.

Characterization of Sensors

Films of alkylamine- and TOABr-coated Pd and Pd alloy nanoparticles were drop-cast deposited onto Si (100)/TiW (50 Å)/Au (2000 Å) and electrode devices for surface reflectance Fourier Transform Infrared (FTIR) spectroscopy and AFM experiments, respectively. FTIR data were acquired using a Digilab FTS 7000 spectrometer (Varian, Cambridge, Mass.) in reflectance mode with a liquid $N_2$-cooled MCT detector. AFM images were acquired with a Veeco Digital Instruments Nanoscope 3A Multimode Scanning Probe Microscope (Santa Barbara, Calif.) using a Si tip operating in tapping mode. $^1$H Proton NMR and UV-vis spectroscopy were obtained with an INOVA 500 MHz and a Varian Cary 50 spectrometer, respectively.

Example 1

Sensor Device

FIG. 1 shows an exemplary device used to test the reactivity of hydrogen with various solid-state films of alkylamine- and tetraoctylammonium bromide-coated Pd, Pd/Ag, and Pd/Au nanoparticles by monitoring changes in conductivity in the presence of various hydrogen concentrations with $N_2$ or air as the carrier gas. The exemplary device depicted in FIG. 1 consists of two Au electrodes with a chromium adhesion layer on a Si/SiOx substrate separated by 23 µm at the closest point, which was fabricated by standard photolithography, sputtering, and lift-off procedures. Frame A shows the device before and Frame B shows the device after drop-cast deposition of a film of $C_8H_{17}NH_2$-coated Pd nanoparticles. The figure also illustrates the various metal compositions (Pd, Pd/Ag, and Pd/Au) and protecting ligands used, which includes hexanethiolate ($C_6H_{13}S$), octylamine ($C_8H_{17}NH_2$), dodecylamine ($C_{12}H_{25}NH_2$), hexadecylamine-octadecylamine ($C_{16}H_{36}NH_2/C_{18}H_{37}NH_2$), and tetraoctylammonium bromide (TOABr).

Example 2

Electronic Properties of Alkylamine- and TOABr-Coated Pd Nanoparticles

FIG. 2A shows the current-voltage (I-V) curves for drop-cast deposited films of $C_8H_{17}NH_2$, $C_{12}H_{25}NH_2$, $C_{16}H_{36}NH_2/C_{18}H_{37}NH_2$, and TOABr-coated Pd nanoparticles. FIG. 2B shows the films of $C_{12}H_{25}NH_2$-coated Pd, $C_{16}H_{36}NH_2/C_{18}H_{37}NH_2$-coated Pd nanoparticles, and background expanded (see dashed box in FIG. 2A). The current through the film of $C_8H_{17}NH_2$-coated Pd nanoparticles is linear with potential, showing ohmic behavior. Current through the film of $C_{12}H_{25}NH_2$-coated Pd nanoparticles is also ohmic, but shows hysteresis because the current is close to the level of the background. The I-V curve for the film of $C_{16}H_{36}NH_2/C_{18}H_{37}NH_2$-coated Pd nanoparticles is very close to the background (with no coated-nanoparticles deposited), indicating little conductivity through this film. The shape of the curves and the fact that the conductivity, which is proportional to the slope of the I-V curve, decreases with increasing chain length is consistent with an electron hopping conductivity mechanism through the films, which depends on the cluster edge-to-edge distance (exponentially), the dielectric of the medium surrounding the clusters, and cluster size, similar to what is observed for films of Au MPCs [45-48].

There is almost no current through the film of $C_{16}H_{36}NH_2/C_{18}H_{37}NH_2$-coated Pd nanoparticles because the cluster edge-to-edge distance is too large for significant electron hopping to occur, which is expected to be greater than 20 Å considering that the distance is estimated to be approximately 1.2 times the chain length of one ligand due to interdigitation of the monolayers from adjacent clusters.

The I-V curve of the film of TOABr-coated Pd nanoparticles is markedly different compared to that of $C_8H_{17}NH_2$-coated Pd nanoparticles. The current is on the same order of magnitude, but the plot does not show ohmic behavior where the current is the same as a function of potential on the forward and reverse scan. Instead, there is large hysteresis on the forward and reverse scan, which is consistent with the current being dominated by ionic current, likely due to the large excess of TOA+ and Br– ions in the film since these nanoparticles could not be purified as a solid.

FIG. 2C shows chronoamperometry (CA) curves in air of films of $C_8H_{17}NH_2$—, $C_{12}H_{25}NH_2$—, $C_{16}H_{36}NH_2/C_{18}H_{37}NH_2$—, and TOABr-coated Pd nanoparticles measured for 1000 s at –0.3 V. For the films of alkylamine-coated Pd nanoparticles, the current is fairly constant over time, consistent with ohmic behavior. The magnitude of current is $5.5\times10^{-9}$ A, $1.0\times10^{-10}$ A, and $2.3\times10^{-11}$ A for films of $C_8H_{17}NH_2$—, $C_{12}H_{25}NH_2$—, $C_{16}H_{36}NH_2/C_{18}H_{37}NH_2$-coated nanoparticles, respectively, showing a decrease in conductivity with increasing chain length. The current displayed by the film of $C_{16}H_{36}NH_2/C_{18}H_{37}NH_2$-coated Pd nanoparticles is again very close to the background with no coated-nanoparticles deposited. The film of TOABr-coated Pd does not show ohmic behavior where the current remains constant with potential over time. Instead, the current decreases from $3.5\times10^{-8}$ A to $2.0\times10^{-10}$ A over 1000 s, which is consistent with a diffusion process and ionic conductivity.

The final conductivity value is above the baseline, which can be due to steady-state ionic conductivity or some electron hopping through the film. The data in FIG. 2 thus shows that films of alkylamine-coated Pd nanoparticles conduct by an electron hopping process and those of TOABr-coated Pd nanoparticles conduct mainly by ions.

Example 3

Figure 2:
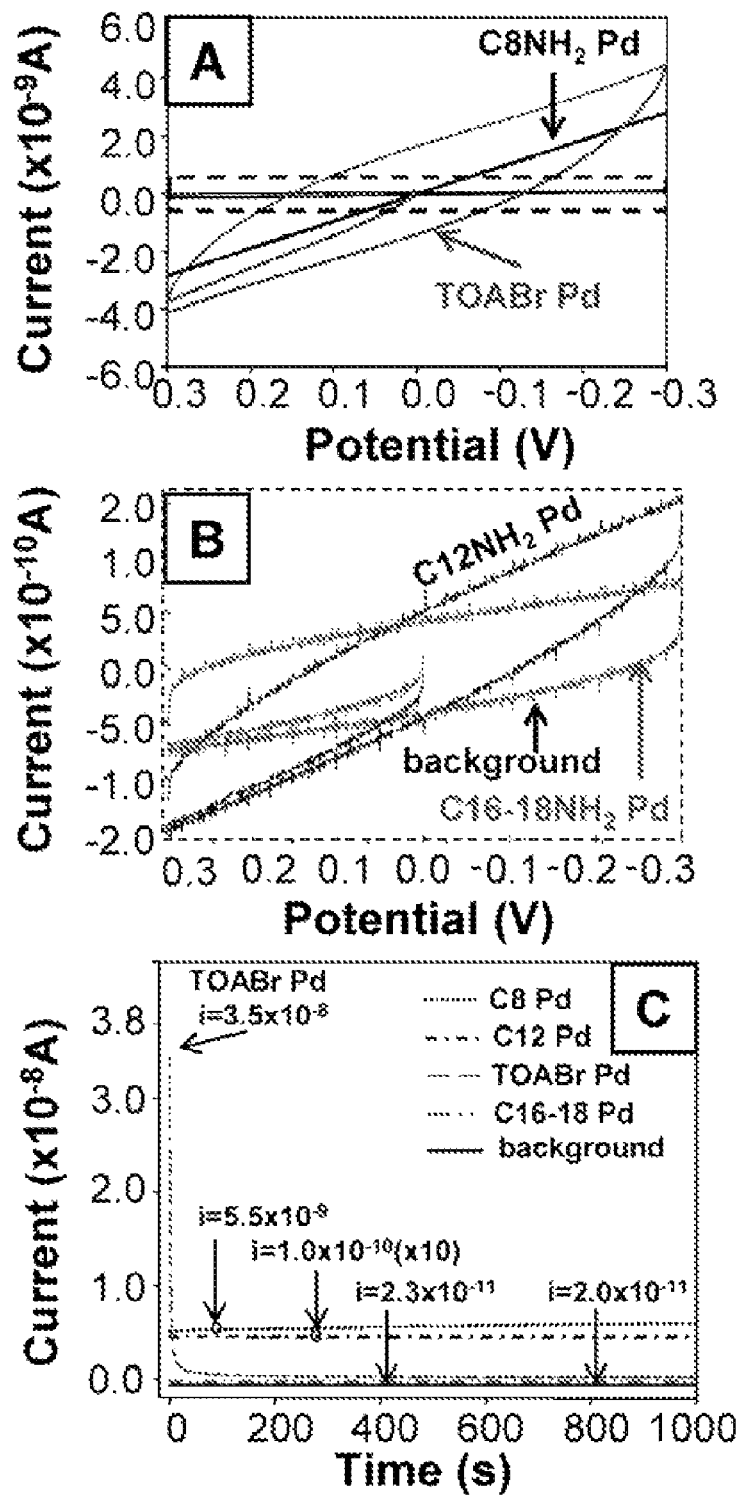
FIGS. 2A-2C are cyclic voltammograms (CV) and chronoamperometry (CA) plots of drop-cast deposited chemiresistant films.
Figure 3:
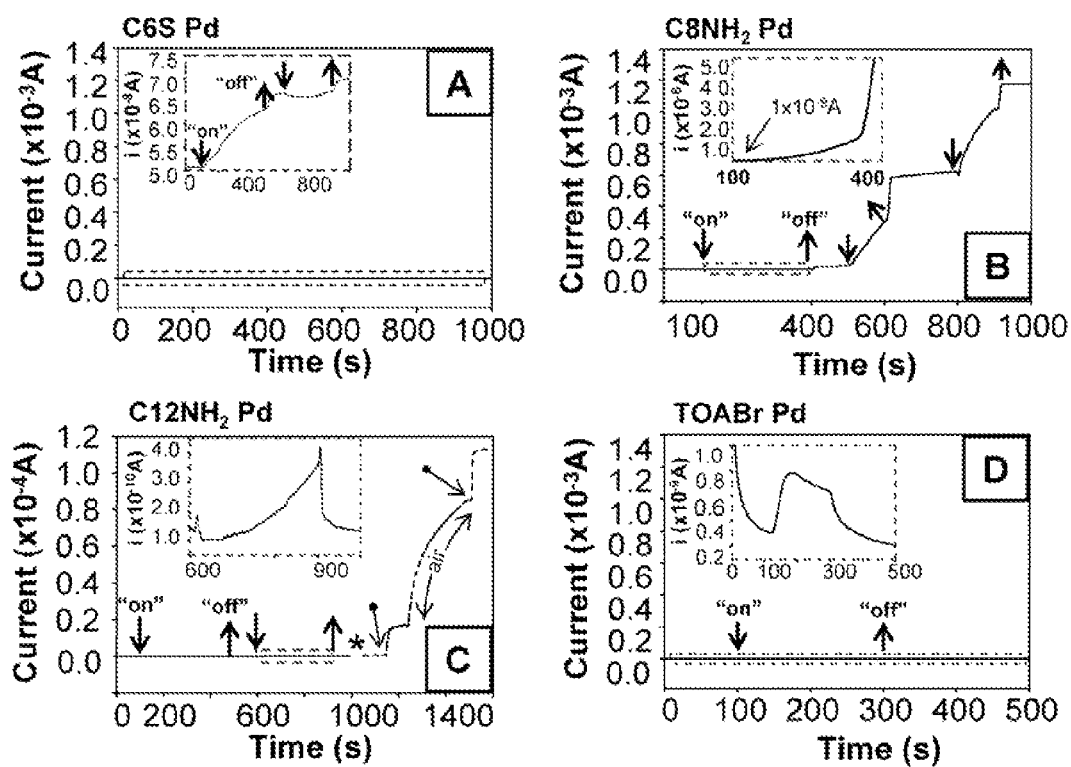
FIGS. 3A-3D are CA plots of films of $C_6H_{13}S$-coated Pd nanoparticles (C6S Pd) (FIG. 3A), $C_8H_{17}NH_2$-coated Pd nanoparticles (C8 $NH_2$ Pd) (FIG. 3B), $C_{12}H_{25}NH_2$-coated Pd nanoparticles (C12 $NH_2$ Pd) (FIG. 3C), and TOABr-coated Pd nanoparticles (TOABr Pd) (FIG. 3D) measured at −0.3 V during repeated exposure to 100% $H_2$ (arrow down) and 100% air (arrow up) during film conditioning to reach stable currents. Insets are expanded plots of the regions indicated by the dashed rectangles. Different type of arrows represent exposure to 9.6% $H_2$ in FIG. 3C.

Reactivity of Films of Alkylamine- and TOABr-Coated Pd Nanoparticles to 100% $H_2$ FIG. 3 shows the current as a function of time flowing through films of $C_6H_{13}S$—, $C_8H_{17}NH_2$—, $C_{12}H_{25}NH_2$—, and TOABr-coated Pd nanoparticles at a voltage of –0.3 V where 100% $H_2$ or 100% air (or $N_2$ for $C_6H_{13}S$—,) is flowing over the sensor device at various times as indicated by $H_2$ "on" (arrow down) and $H_2$ "off" (arrow up), respectively. Films of $C_{16}H_{36}NH_2/C_{18}H_{37}NH_2$-coated Pd nanoparticles had very little conductivity and did not change in the presence of 100% $H_2$ for up to 2000 s and therefore are not shown in FIG. 3. The current is stable for $C_6H_{13}S$—, $C_8H_{17}NH_2$—, $C_{12}H_{25}NH_2$-coated Pd nanoparticles in 100% air initially as also shown in FIG. 2. In the presence of 100% $H_2$, FIG. 3A shows that the current passing through a selected film of $C_6H_5S$-coated Pd nanoparticles changed irreversibly from about $5.0\times10^{-8}$ to $7.0\times10^{-8}$ A over a 1000 s period (see inset for expanded plot). This small, irreversible change in current reflects very little reactivity with $H_2$, which was determined to be due to poisoning of the reaction between Pd and $H_2$ by the strongly coordinated thiolates surrounding the Pd nanoparticles [49]. Ozone- and heat-induced removal of $C_6H_{13}S$— leads to much greater reactivity with $H_2$ and reversible sensing characteristics [49].

In contrast to $C_6H_5S$-coated Pd nanoparticles, the conductivity of films of $C_8H_{17}NH_2$— and $C_{12}H_{25}NH_2$-coated Pd nanoparticles change much more appreciably in the presence of 100% $H_2$ without any ozone or heat pre-treatment. FIG. 3B shows that the current passing through a film of $C_8H_{17}NH_2$-coated Pd nanoparticles increased irreversibly from about $1\times10^{-9}$ A to $5\times10^{-6}$ A during the first 300 s exposure (see inset). The current continued to rise slightly when in 100% air and then increased to $5.0\times10^{-4}$ A upon the second $H_2$ exposure. This trend continued until the film reached a final current of $1.2\times10^{-3}$ A. The current passing through the film of $C_8H_{17}NH_2$-coated Pd nanoparticles overall increased by 6 orders of magnitude during the 1000 s of various exposures to $H_2$ and air whereas the film of $C_6H_{13}S$-coated Pd nanoparticles only increased by a factor of 1.4. This indicates that the more weakly coordinated octylamines do not hinder the Pd from reacting with $H_2$. The irreversible increase in current over the 1000 s is likely due to restructuring of the Pd film during repeated exposure and removal from 100% $H_2$, which is well-known to occur for Pd materials [6].

FIG. 3C shows the current passing through a film of $C_{12}H_{25}NH_2$-coated Pd nanoparticles upon different exposures to 100% $H_2$ and air. In this case, the current increased from about $1\times10^{-10}$ to about $4\times10^{-10}$ during the first 400 s exposure to $H_2$ and reversibly returned close to the baseline. Upon the second 300 s exposure, the current increased similarly and again returned close to the baseline upon removal from $H_2$ (see inset). This increase in current is similar to the increase for films of $C_6H_{13}S$-coated Pd nanoparticles, but the behavior is reversible. The asterisk in the plot indicates that sensing was performed at this time (vide infra). At a later time, around 1150 s, the current exhibited a much larger increase to about $2\times10^{-5}$ A and then finally to a stable value of about $1.2\times10^{-4}$ A. The films of $C_{12}H_{25}NH_2$-coated Pd nanoparticles are similar to those of $C_8H_{17}NH_2$-coated Pd nanoparticles in that they irreversibly increase in current to a value about 6 orders of magnitude higher than the initial current.

The increase in current can be due to film restructuring in both cases, but the kinetics are different for the two films. Films of $C_8H_{17}NH_2$-coated Pd nanoparticles restructure and stabilize in a more continuous step which is less than 1000 s, while films of $C_{12}H_{25}NH_2$-coated Pd nanoparticles initially show a somewhat stable, reversible response to $H_2$ that changes to a large, irreversible increase in current at times greater than 1000 s. The longer time required to reach the higher current is likely due to the longer alkyl chains slowing down the reaction and film restructuring process. The final restructured film for the $C_{12}H_{25}NH_2$-coated Pd nanoparticles has a higher final resistance compared to the restructured film of $C_8H_{17}NH_2$-coated Pd nanoparticles.

FIG. 3D shows the current passing through a film of TOABr-coated Pd nanoparticles upon exposure to 100% $H_2$ and air. These films exhibited stable, reversible increases in current in the presence of 100% $H_2$ immediately and did not require any conditioning (see inset).

Table 1 summarizes the results of the conditioning during initial exposure to 100% $H_2$ for films comprised of $C_8H_{17}NH_2$—, $C_{12}H_{25}NH_2$—, $C_{16}H_{36}NH_2/C_{18}H_{37}NH_2$—, and TOABr-coated pure Pd nanoparticles. The table displays the average initial current, time it took for the current to increase by one order of magnitude during initial exposure to 100% $H_2$, total time it took in (s) to reach the final stable current, and the final stable current after conditioning. Standard deviations and ranges are based on three samples for each type of Pd film studied. The initial current reflects the chain length dependence on electron hopping conductivity, except for TOABr-coated Pd films, which conduct ionically.

TABLE 1

Conditioning for films of pure Pd nanoparticles.

| Film | Initial current (A) | Time for 1 order of mag. increase in current (s) | Time current reached stable value (s) | $1^{st}$ Condit. Final current (A) | $2^{nd}$ Condit. Final current (A) |
|---|---|---|---|---|---|
| C8NH$_2$ Pd | $7.0 \times 10^{-10} - 3.0 \times 10^{-9}$ | 93 ± 42 | 467 ± 55 | $2.4 \times 10^{-4} - 1.8 \times 10^{-3}$ | / |
| C12NH$_2$ Pd | $1.0 \times 10^{-10} - 2.5 \times 10^{-10}$ | 933 ± 513 | 1083 ± 448 | $1.0 \times 10^{-9} - 7.5 \times 10^{-9}$ | $5.4 \times 10^{-4} - 3.0 \times 10^{-3}$ |
| C18-16NH$_2$ Pd | $4.0 \times 10^{-11}$ | / | / | / | / |
| TOABr Pd | $5.0 \times 10^{-9} - 4.0 \times 10^{-8}$ | / | / | / | / |

Table 1 shows that the time to reach an increase of one order of magnitude in current is about 10 times quicker for films of $C_8H_{17}NH_2$-coated Pd nanoparticles compared to those of $C_{12}H_{25}NH_2$-coated Pd nanoparticles and the total time to reach a final stable current is longer for films of $C_{12}H_{25}NH_2$-coated Pd nanoparticles. Films of $C_{12}H_{25}NH_2$-coated Pd nanoparticles also displayed two different changes in current. Films of $C_{16}H_{36}NH_2/C_{18}H_{37}NH_2$-coated Pd and TOABr-coated Pd nanoparticles do not have any data because the former responds little to $H_2$ and the latter does not require any conditioning for stable, reversible responses.

Example 4

$H_2$ Sensing with Films of Alkylamine- and TOABr-Coated Nanoparticles

Figure 4:
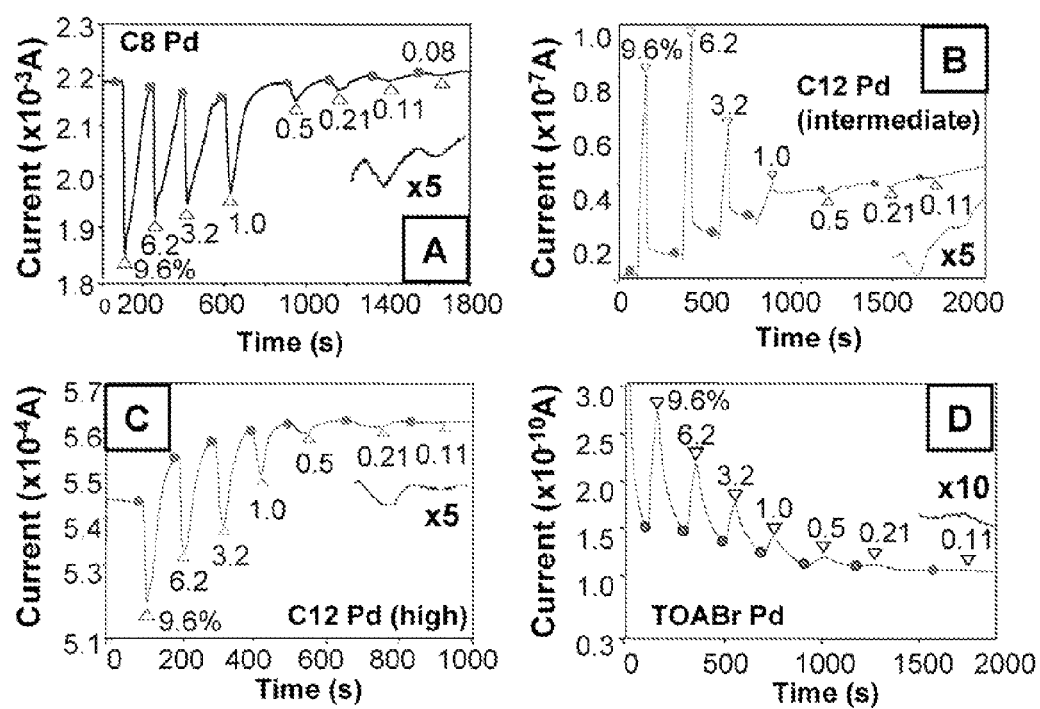
FIGS. 4A-4D are CA plots of films of $C_8H_{17}NH_2$-coated Pd nanoparticles (C8 Pd) (FIG. 4A), $C_{12}H_{25}NH_2$-coated Pd nanoparticles (C12 Pd) (intermediate current) (FIG. B), $C_{12}H_{25}NH_2$-coated Pd nanoparticles (high current) (FIG. 4C), and TOABr-coated Pd nanoparticles (TOABr Pd) (FIG. 4D) exposed to $H_2$ concentrations from 9.6 to 0.08% as indicated in $N_2$ carrier gas. The films were initially exposed to 100% $N_2$ and the circles represent the point of exposure to the $H_2$ concentration indicated and open triangles represent the point of exposure back to 100% $N_2$

FIG. 4 shows chronoamperometry (CA) plots of current versus time for selected films of $C_8H_{17}NH_2$—, $C_{12}H_{25}NH_2$—, and TOABr-coated Pd nanoparticles that were exposed to $H_2$ concentrations from 9.6% down to 0.08% $H_2$. "$H_2$ off" correlates with exposures to 100% $N_2$ and "$H_2$ on" correlates with exposure to $H_2$ at the percent indicated in a $H_2/N_2$ mixture. The sensing behavior in FIG. 4 was measured after conditioning the films to obtain a stable, reversible response to $H_2$, except for films of TOABr-coated Pd nanoparticles, which did not require conditioning. FIG. 4A shows that the film of $C_8H_{17}NH_2$-coated Pd nanoparticles exhibited a very sharp and reversible decrease in current in the presence of 9.6% to 1.0% $H_2$. The decrease in current is less pronounced below 1.0% $H_2$, but did show a noticeable response to concentrations as low a 0.08% $H_2$ for a 100 s exposure. FIGS. 4B and 4C show the chemiresistive response to $H_2$ for a selected film of $C_{12}H_{25}NH_2$-coated Pd nanoparticles after the first and second conditioning event, respectively, as discussed above with regard in FIG. 3.

After the first conditioning (see the * in FIG. 3C), the current through the film is on the order of $10^{-8}$ A and the current increases in the presence of $H_2$ down to 1.0%, but decreases for lower $H_2$ concentrations down to 0.11%. The response for this film is not totally reversible as indicated by the constantly shifting baseline current to higher values, which is undesirable for sensing. The unstable current is due to attempts of film calibration at this stage of current indicated by the arrows (different type) in FIG. 3C. FIG. 4C shows the current response of the same film after it reached a higher, stable baseline current on the order of $10^{-4}$ A. The response completely changed, where the current decreased in the presence of $H_2$ down to concentrations of 0.11%, similar to films of $C_8H_{17}NH_2$-coated Pd nanoparticles. FIG. 4D shows the change in current of a selected film of TOABr-coated Pd nanoparticles in the presence of $H_2$. The film exhibited a stable, reversible increase in current in the presence of $H_2$ concentrations ranging from 9.6 down to 0.11% without any pretreatment or film conditioning. There is a slight drift in the baseline to smaller current over time due to a drop in the baseline ionic conductivity with time as shown in FIG. 2.

FIG. 4 shows two different types of sensing behavior: those that decrease in conductivity and those that increase in conductivity in the presence of $H_2$. Films of $C_8H_{17}NH_2$-coated Pd (C8NH$_2$ Pd) nanoparticles and $C_{12}H_{25}NH_2$-coated Pd nanoparticles (after second conditioning) have baseline currents on the order of $10^{-3}$ and $10^{-4}$ A and decrease in current in the presence of $H_2$, which is consistent with what has been observed previously for well-connected, low resistance Pd materials [6,7]. The decrease in current is due to the increased resistance of the PdHx formed in the presence of $H_2$ compared to pure Pd [38]. Films of $C_{12}H_{25}NH_2$-coated Pd (C12NH$_2$ PdAg) nanoparticles after the first conditioning have a relatively smaller baseline current on the order of $10^{-8}$ A and the current increases in the presence of $H_2$ at concentrations greater than 1.0%. The Pd nanoparticles in these films are not well-connected and the expansion in volume of the Pd when forming PdHx leads to an overall decrease in resistance due to closer spacing or formation of connections between particles [9]. A decrease in the current in the presence of $H_2$ at concentrations lower than 0.50% was observed for these films. This can be attributed to a temporary increase in resistance upon low amounts of H diffusing into α-phase Pd at low $H_2$ concentration [12]. Eventually, the resistance of the film should decrease once the expanded β-phase Pd forms. Without wishing to be bound by theory, it is believed that the slow kinetics of this process at low $H_2$ concentration leads to the observed reduction in current and that the current would have eventually increased if the film were exposed to $H_2$ at these low concentrations for longer time. Even at higher concentrations ($\geqq 1.0\%$), an initial drop in current occurs first, but the Pd phase change kinetics are faster and the current eventually increases on the timescale of the exposure. The increase in current for films of TOABr-coated Pd nanoparticles is because those films conduct ionically, but there may be some electron hopping as well. The formation of PdHx leads to higher currents, which could be related to closer spacing of particles upon expansion in volume. It could also be related to increased thermal motions upon H or $H_2$ adsorption into the films similar to the increase in current observed for films of $C_6H_{13}S$-coated Au nanoparticles in the presence of $CO_2$ gas [50]. More experiments are needed to better understand the mechanism. We also observed an increase in conductivity for TOABr-coated Au nanoparticles in the presence of $H_2$, but the Pd metal plays an important role since films of TOABr-coated Pd were much more sensitive, stable, and reversible.

Example 5

Reactivity of Alkylamine- and TOABr-Coated Pd/Ag and Pd/Au Nanoparticles to 100% $H_2$ The response to hydrogen for films of Pd/Ag and Pd/Au alloy nanoparticles was next determined. These alloys are significant because Ag is cheaper than Pd, which could reduce the cost of sensors or catalysts based on these materials. From a chemical standpoint, Pd/Ag has been shown to be more sensitive since Ag can adsorb more H into its lattice and Pd/Au alloys have shown faster response times due to Au hindering the α-β phase transition during H diffusion into Pd [25-27]. I-V curves obtained on films of the alloy nanoparticles were very similar to those of the pure Pd and are not shown. FIG. 5A shows the change in current for a film of $C_8H_{17}NH_2$-coated Pd/Ag nanoparticles when first exposed to 100% $H_2$. The current increased in the presence of 100% $H_2$ from about $1.0 \times 10^{-10}$ A to $1.2 \times 10^{-8}$ A, which is approximately 2 orders of magnitude. This is significantly different from the 6 order of magnitude increase observed for pure Pd films (see FIG. 3). The presence of less than 10% Ag in the alloy led to much higher resistance in the film following restructuring in 100% $H_2$. Similarly-prepared films of $C_{12}H_{25}NH_2$-coated Pd/Ag (C12NH$_2$ PdAg) films exhibited very low baseline currents and did not change significantly in the presence of 100% $H_2$. FIG. 5B shows the change in current for a film of $C_{12}H_{25}NH_2$-coated Pd/Au (C12NH$_2$ PdAu) nanoparticles in the presence of 100% $H_2$. In contrast to films of $C_{12}H_{25}NH_2$-coated Pd/Ag nanoparticles, the $C_{12}H_{25}NH_2$-coated Pd/Au film exhibited a dramatic jump in current to $10^{-7}$ A in about 300 s and eventually increased to about $1.0 \times 10^{-4}$ A, similar to films of $C_{12}H_{25}NH_2$-coated pure Pd nanoparticles.

One difference between the Pd/Au alloy and pure Pd is that the current constantly increased in ambient air upon only one exposure to 100% $H_2$, whereas pure Pd showed some initial reversibility to $H_2$ during the first exposures. As with films of TOABr-coated Pd, films of TOABr-coated Pd/Ag exhibited stable, reversible increases in current immediately in the presence of 100% $H_2$. Table 2 summarizes the behavior of the various films of Pd alloy nanoparticles that were conditioned with 100% $H_2$ and air. The table displays the same parameters shown in Table 1 and reflects the smaller and slower current increase for Pd/Ag alloys and the faster, larger increase for Pd/Au alloys. Again, TOABr-coated Pd/Ag does not show any data because it does not require any conditioning for stable, reversible responses.

TABLE 2

Conditioning data for films of Pd alloy nanoparticles.

| Film | Initial current (A) | Time for 1 order of mag. increase in current (s) | Time current reached stable value (s) | Final current (A) |
| --- | --- | --- | --- | --- |
| C8NH$_2$ PdAg | $1.2 \times 10^{-10} - 1.5 \times 10^{-9}$ | 413 ± 23 | 433 ± 58 | $7.0 \times 10^{-9} - 4.0 \times 10^{-8}$ |
| C12NH$_2$ PdAu | $1.0 \times 10^{-10} - 1.8 \times 10^{-10}$ | 110 ± 10 | 300 ± 20 | $2.0 \times 10^{-4} - 6.2 \times 10^{-4}$ |
| TOABr PdAg | $5.0 \times 10^{-9} - 4.0 \times 10^{-8}$ | / | / | / |

Example 6

H$_2$ Sensing with Films of Pd Alloy Nanoparticles

Figure 5:
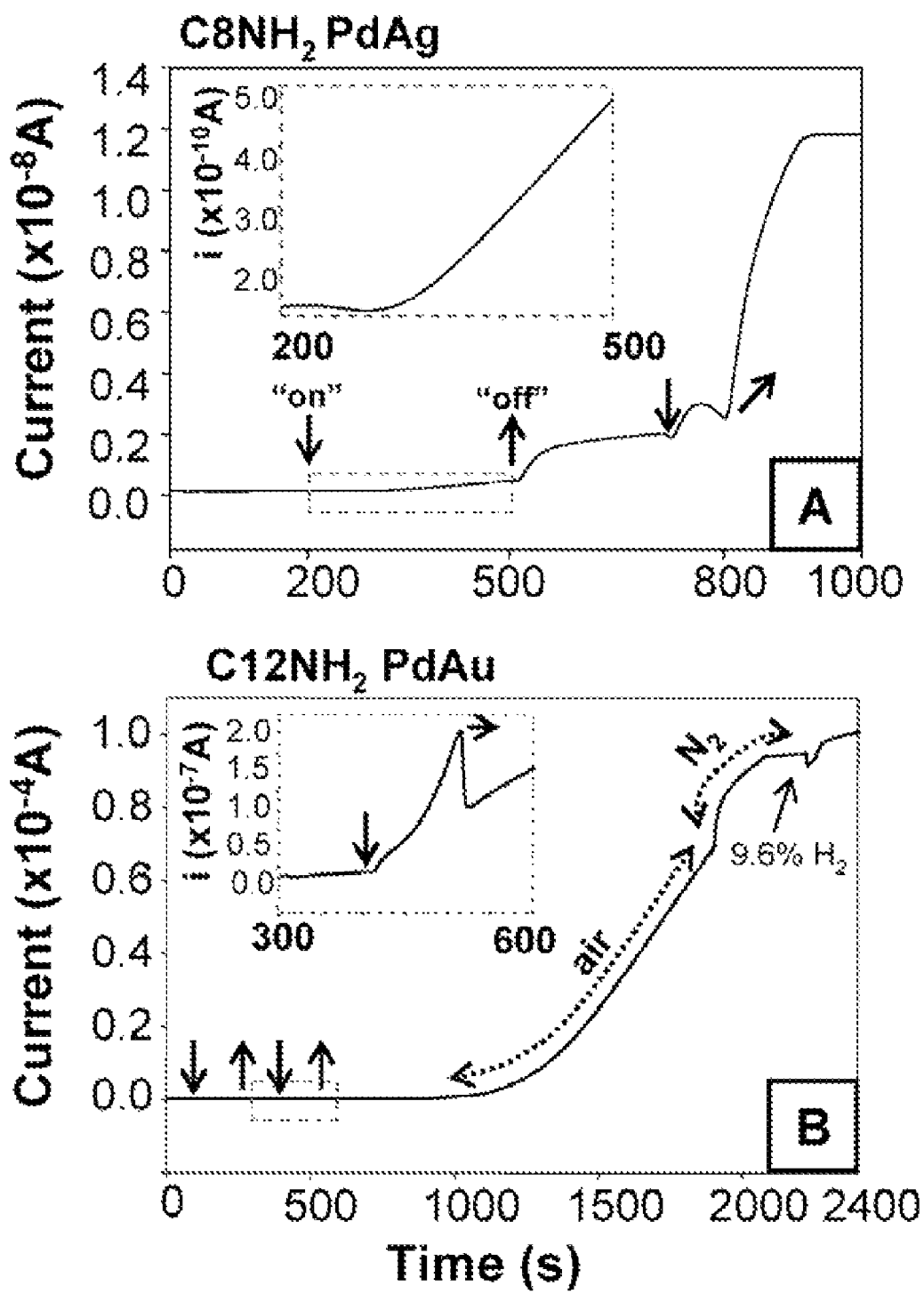
FIGS. 5A and 5B are CA plots of films of $C_8H_{17}NH_2$-coated Pd/Ag nanoparticles (C8 $NH_2$ PdAg) (FIG. 5A) and $C_{12}H_{25}NH_2$-coated Pd/Au nanoparticles (C12 $NH_2$ PdAu) (FIG. 5B) measured at −0.3 V during repeated exposure to 100% $H_2$ (arrow down) and 100% air (arrow up) during film conditioning to reach stable currents. Insets are expanded plots of the regions indicated by the dashed rectangles.
Figure 6:
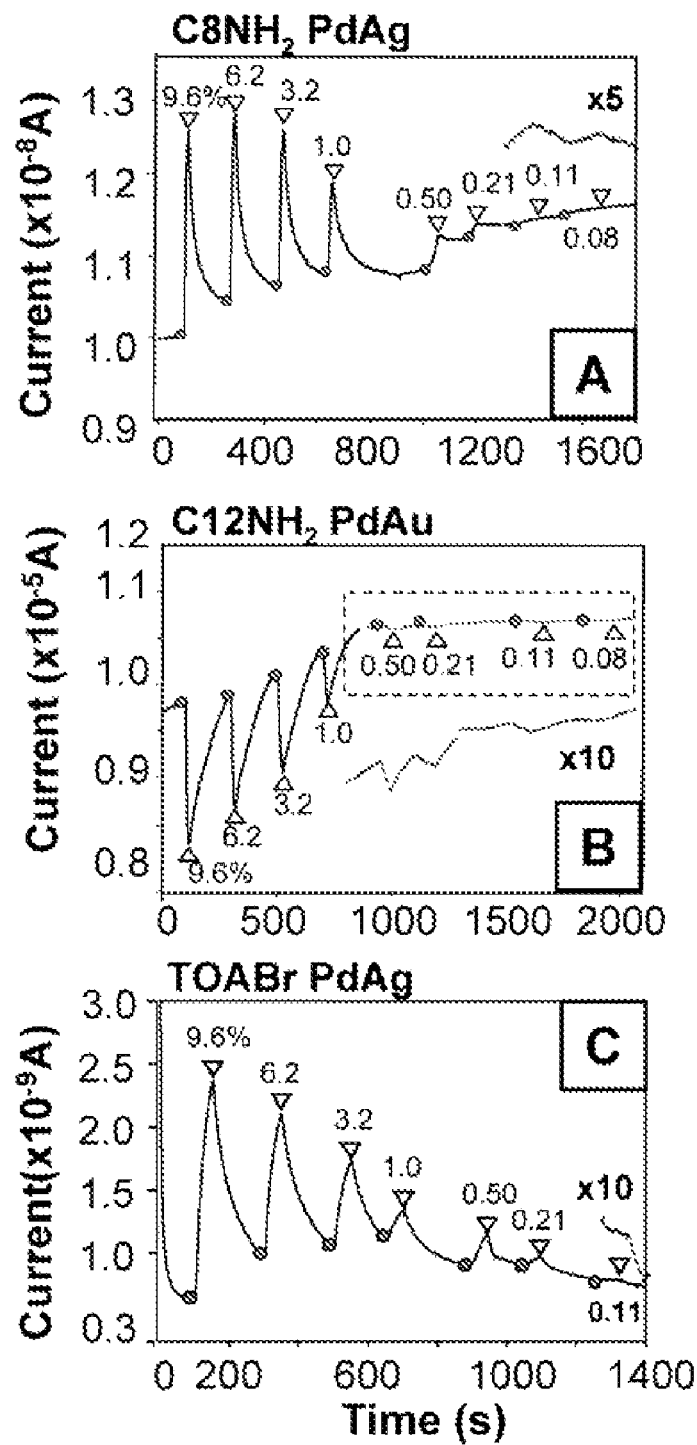
FIGS. 6A-6C are CA plots of films of $C_8H_{17}NH_2$-coated Pd/Ag nanoparticles (C8 $NH_2$ PdAg) (FIG. 6A), $C_{12}H_{25}NH_2$-coated Pd/Au nanoparticles (C12 $NH_2$ PdAu) (FIG. 6B), and TOABr-coated Pd/Ag nanoparticles (TOABr PdAg) (FIG. 6C) exposed to $H_2$ concentrations from 9.6 to 0.08% as indicated in $N_2$ carrier gas. The films were initially exposed to 100% $N_2$ and the circles represent the point of exposure to the $H_2$ concentration indicated and open triangles represent the point of exposure back to 100% $N_2$.

FIG. 6 shows the chemiresistive response to H$_2$ for selected films of C$_8$H$_{17}$NH$_2$-coated Pd/Ag nanoparticles, C$_{12}$H$_{25}$NH$_2$-coated Pd/Au, and TOABr-coated Pd/Ag nanoparticles following the conditioning to stable baseline currents as discussed with regard to FIG. 5. Having a low initial conductivity (approximately $10^{-8}$ A), the current for films of C$_8$H$_{17}$NH$_2$-coated Pd/Ag nanoparticles increased in the presence of H$_2$ concentrations from 9.6 to 0.08% (FIG. 6A). This is different from films of C$_8$H$_{17}$NH$_2$-coated pure Pd nanoparticles (FIG. 4A), which have a larger stable baseline current after conditioning ($10^{-4}$ A) that decreased in the presence of H$_2$. The addition of less than 10% Ag altered the film restructuring process upon initial exposure to 100% H$_2$ and the H$_2$ sensing mechanism.

FIG. 6B shows the change in current for a selected film of C$_{12}$H$_{25}$NH$_2$-coated Pd/Au nanoparticles during exposure to H$_2$. The baseline current is on the order of $10^{-5}$ A and the current decreased in the presence of 9.6 to 0.08% H$_2$ similar to films of C$_8$H$_{17}$NH$_2$-coated Pd and C$_{12}$H$_{25}$NH$_2$-coated Pd nanoparticles after the second conditioning, but very different from films of C$_{12}$H$_{25}$NH$_2$-coated Pd/Ag nanoparticles, which did not respond to H$_2$. FIG. 6C shows the change in current for a film of TOABr-coated Pd/Ag nanoparticles. The current increased in the presence of 9.6 to 0.11% H$_2$ and is indistinguishable from films of TOABr-coated pure Pd nanoparticles (FIG. 4C).

In contrast to films of alkylamine-coated nanoparticles, the reactivity of TOABr-coated nanoparticles with H$_2$ is insensitive to the metal composition for the ratio studied. The explanation for the different types of sensing (increase and decrease in current) is the same as that described for the films of pure Pd nanoparticles.

Example 7

Surface FTIR Spectroscopy Characterization

Fourier Transform Infrared (FTIR) spectroscopy was used to probe the organic portion of the films before and after exposure to H$_2$ to gain insight into the film restructuring process and sensing mechanism. FIGS. 7A-7D, show surface FTIR spectra for selected films of C$_8$H$_{17}$NH$_2$-coated Pd, C$_8$H$_{17}$NH$_2$-coated Pd/Ag, C$_{12}$H$_{25}$NH$_2$-coated Pd, and C$_{12}$H$_{25}$NH$_2$-coated Pd/Au nanoparticles, respectively, before and after exposure to 100% H$_2$ that were placed in the same cell as electrodes containing the same films for conductivity measurements. Before exposure, all of the spectra show absorbance peaks similar to those previously reported for alkylamine monolayers on Pd [51] and Au [43]. For example, the spectrum for the film of C$_8$H$_{17}$NH$_2$-coated Pd nanoparticles before H$_2$ exposure displays absorbances at 3280 cm$^{-1}$, 1604 cm$^{-1}$, and 1000 cm$^{-1}$, which corresponds to the N—H stretch, N—H bend, and C—N stretch, respectively, as indicated [43].

The peaks at 3000-2850 cm$^{-1}$ are due to the asymmetric and symmetric CH$_3$ and CH$_2$ stretches and the peak at 1462 cm$^{-1}$ is due to a CH$_2$ scissor mode, as indicated. In addition, a sharp peak was observed at 2167 cm$^{-1}$, which is in the region of a C≡N or C≡C stretching vibration. Without wishing to be bound by theory, this is likely due to a C≡N stretch that arises from converting the R—CH$_2$—NH$_2$ to a R—C≡N by oxidation of amines catalyzed by Pd during the synthesis. This peak was assigned to the terminal isocyanide ligand. The spectra also showed peaks at approximately 1964 (2100-1700 cm$^{-1}$) and approximately 1611 (1700-1500 cm$^{-1}$), which was assigned to a doubly-bridged, and triply-bridged isocyanide ligand to Pd, respectively [5]. The spectra are mostly featureless in these regions before H$_2$ exposure.

FIG. 7A shows the FTIR spectrum of a film of C$_8$H$_{17}$NH$_2$-coated Pd nanoparticles before and after exposure to 100% H$_2$ for 500 s corresponding to currents of $3.2 \times 10^{-9}$ A and $1.4 \times 10^{-3}$ A, respectively. There are four main changes in the spectrum following exposure to H$_2$ and increase in current. First, the intensity of the CH$_2$ and CH$_3$ stretches decreased significantly. In particular, the peak height of the asymmetric CH$_2$ stretch decreased by 80%. FIG. 3 earlier showed that the film restructures and increases in conductivity upon the first exposure to 100% H$_2$. The IR data show that the alkylamines are removed from the film during this restructuring process. The second change in the spectrum is the loss of the peak at 2167 cm$^{-1}$. If this peak is C≡N as believed, then the nitriles can be reduced to amines in the presence of Pd and H$_2$ [52]. The third change is a sharpening and slight shift to a higher wavenumber for the N—H bend at around 1600 cm$^{-1}$. The fourth change is that the broad peak at 3280 cm$^{-1}$, ascribed to the NH$_2$ stretch, decreased in intensity and became three sharp peaks. These latter difference show a change occurs in the coordination environment between the R—NH$_2$ and Pd upon exposure to H$_2$. This can be expected considering many of the alkylamines desorbed from the surface and could cause orientation changes and differences in hydrogen bonding and other interactions for the remaining alkylamines. The peak at higher wavenumbers is consistent with non-hydrogen bonded amines as observed in dilute solutions [53].

FIG. 7B shows the FTIR spectrum of a film of C$_8$H$_{17}$NH$_2$-coated Pd/Ag nanoparticles before and after exposure to 100% H$_2$ for 400 s corresponding to currents of $1.2 \times 10^{-10}$ A and $7.0 \times 10^{-9}$ A, respectively. The spectrum has some small differences compared to the film of C$_8$H$_{17}$NH$_2$-coated Pd nanoparticles before exposure to H$_2$. First, the peak attributed to nitriles at 2167 cm$^{-1}$ is much smaller in intensity and there are two sharp peaks in the NH$_2$ stretching region as opposed to one broad peak. Adding less than 10% Ag to the reaction reduced the formation of nitriles and changed the coordination environment of the amines, thus potentially indicating that many of the Ag atoms reside at the surface of the nanoparticles [55]. After exposure to $H_2$, the spectrum is drastically different compared to pure Pd. Most notably, the intensity of the $CH_2$ and $CH_3$ stretches slightly decreased (only 4% for the asymmetric $CH_2$ stretch) and there is a new peak that appears near 1700 $cm^{-1}$. Similar to pure Pd, the nitrile peak disappeared and a third peak appeared at higher wavenumbers in the $NH_2$ stretching region. This peak is the lowest in intensity out of the three peaks for the film of coated Pd/Ag nanoparticles after $H_2$, but is the largest in intensity for the films of coated Pd nanoparticles.

FIG. 7C shows the FTIR spectrum of a film of $C_{12}H_{25}NH_2$-coated Pd nanoparticles before $H_2$, right after the first conditioning (total 800 s in 100% $H_2$), and after the second conditioning (film tested from 9.6 to 0.08% $H_2$) until the film reached stability. The corresponding currents are $3.0 \times 10^{-8}$ A, $1.0 \times 10^{-9}$ A, and $6.2 \times 10^{-4}$ A, respectively. The spectrum looks very similar to that of the film of $C_8H_{17}NH_2$-coated Pd nanoparticles before $H_2$ exposure, where the $NH_2$ stretch is broad and there is a noticeable absorbance band attributed to nitriles. After the first conditioning event, there is a small 12% decrease in the asymmetric $CH_2$ stretch and after the second conditioning/restructuring, there is a 36% loss of this peak. The $NH_2$ peaks remained fairly broad with the presence of a small broad peak appearing around 3313 $cm^{-1}$, instead of splitting into three sharp peaks as observed for films of $C_8H_{17}NH_2$-coated Pd nanoparticles. Another similarity to films of $C_8H_{17}NH_2$-coated Pd nanoparticles is that the nitrile peak disappears.

FIG. 7D shows the FTIR spectrum of a film of $C_{12}H_{25}NH_2$-coated Pd/Au nanoparticles before and after conditioning with 100% $H_2$ for 300 s corresponding to currents of $1.8 \times 10^{-10}$ A and $6.0 \times 10^{-4}$ A, respectively. The spectrum before $H_2$ is similar to the film of $C_{12}H_{25}NH_2$-coated Pd nanoparticles, except that there is no evident peak for the nitrile at 2167 $cm^{-1}$. As with Ag, this shows that the presence of less than 10% Au affected the ability of Pd to catalyze the formation of nitriles. There are also small differences in the $NH_2$ stretching and bending region. After exposure to $H_2$, the spectrum looks very similar to the spectrum for the film of $C_8H_{17}NH_2$-coated Pd nanoparticles. The asymmetric $CH_2$ stretched decreased by approximately 62% and the initially broad peak for the $NH_2$ stretch split into three sharper peaks.

Figure 7:
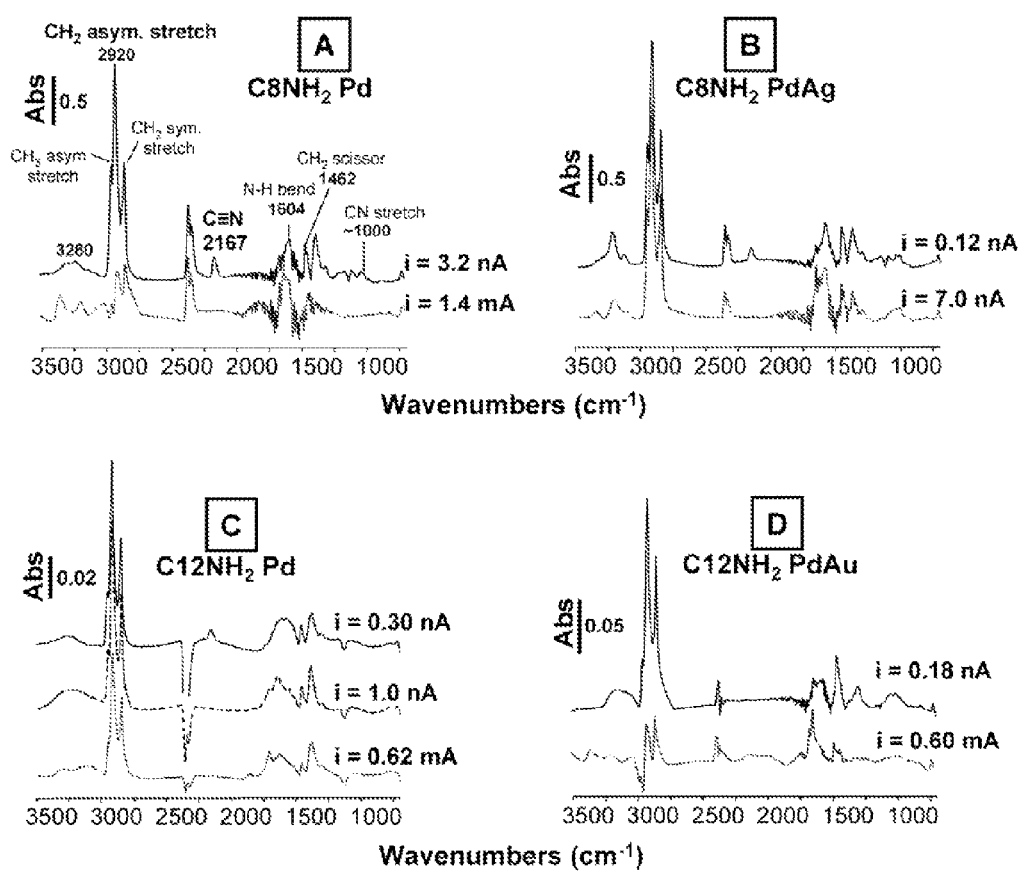
FIGS. 7A-7D are surface Fourier Transform Infrared (FTIR) spectra of films of $C_8H_{17}NH_2$-coated Pd (C8 $NH_2$ Pd) (FIG. 7A), $C_8H_{17}NH_2$-coated Pd/Ag (C8 $NH_2$ PdAg) (FIG. 7B), $C_{12}H_{25}NH_2$-coated Pd (C12 $NH_2$ Pd) (FIG. 7C), and $C_{12}H_{25}NH_2$-coated Pd/Au nanoparticles (C12 $NH_2$ PdAu) (FIG. 7D) obtained before and after exposure to 100% $H_2$ until they reached stable currents. Films were exposed to 100% $H_2$ for a total time of 500 s, 400 s, 800 s, and 300 s, for (A)-(D), respectively. The number displayed next to each spectrum is the current (in amps) passing through similarly prepared films deposited onto electrodes and exposed to $H_2$ in parallel with the FTIR samples. The films of $C_{12}H_{25}NH_2$-coated Pd nanoparticles shows two FTIR spectra after exposure to $H_2$ that correspond to conditioning to intermediate current and high current.

Taken together with the current data and with regard to the data presented in FIGS. 3 and 5, FIG. 7 shows a strong correlation between monolayer desorption and change in film conductivity during the first exposure to 100% $H_2$. Films of $C_8H_{17}NH_2$-coated Pd nanoparticles, $C_{12}H_{25}NH_2$-coated Pd/Au nanoparticles, and $C_{12}H_{25}NH_2$-coated Pd nanoparticles (second conditioning) increased in conductivity by 5-6 orders of magnitude after a 500 s, 300 s, and >800 s exposure, respectively, and showed a correspondingly large loss of the alkylamine monolayer in the IR spectra (80, 62, and 32%, respectively). In addition, the nitriles were reduced to amines (for pure Pd) and the coordination environment of the $NH_2$ groups was altered. This shows that monolayer desorption and changes accompany film restructuring and conductivity increases. Films of $C_8H_{17}NH_2$-coated Pd/Ag nanoparticles and $C_{12}H_{25}NH_2$-coated Pd nanoparticles (first conditioning) showed a much smaller 1-2 order of magnitude conductivity change after 400 s and 800 s, respectively, and a correspondingly much smaller loss of alkylamines from the surface (4 and 12%, respectively). Small changes in the spectrum include loss of the nitrile peak and changes in the $NH_2$ stretch. The IR and conductivity data show that for pure Pd, the longer $C_{12}H_{25}NH_2$— monolayer enhances stability and reduces the reactivity to 100% $H_2$. The presence of less than 10% Ag enhanced stability of the monolayer and reduced the amount of film restructuring for $C_8H_{17}NH_2$-coated nanoparticles compared to pure Pd while the presence of less than 10% Au reduced monolayer stability and increased the restructuring for $C_{12}H_{25}NH_2$-coated nanoparticles compared to pure Pd. This can be due to stronger bonding between alkylamines and Pd/Ag as compared to alkylamines and Pd/Au. Previous studies showed that alkylamine-coated Au nanoparticles are not stable in air [43], while the present data indicates that pure Pd is stable.

Example 8

Atomic Force and Optical Microscopy Characterization

Figure 8:
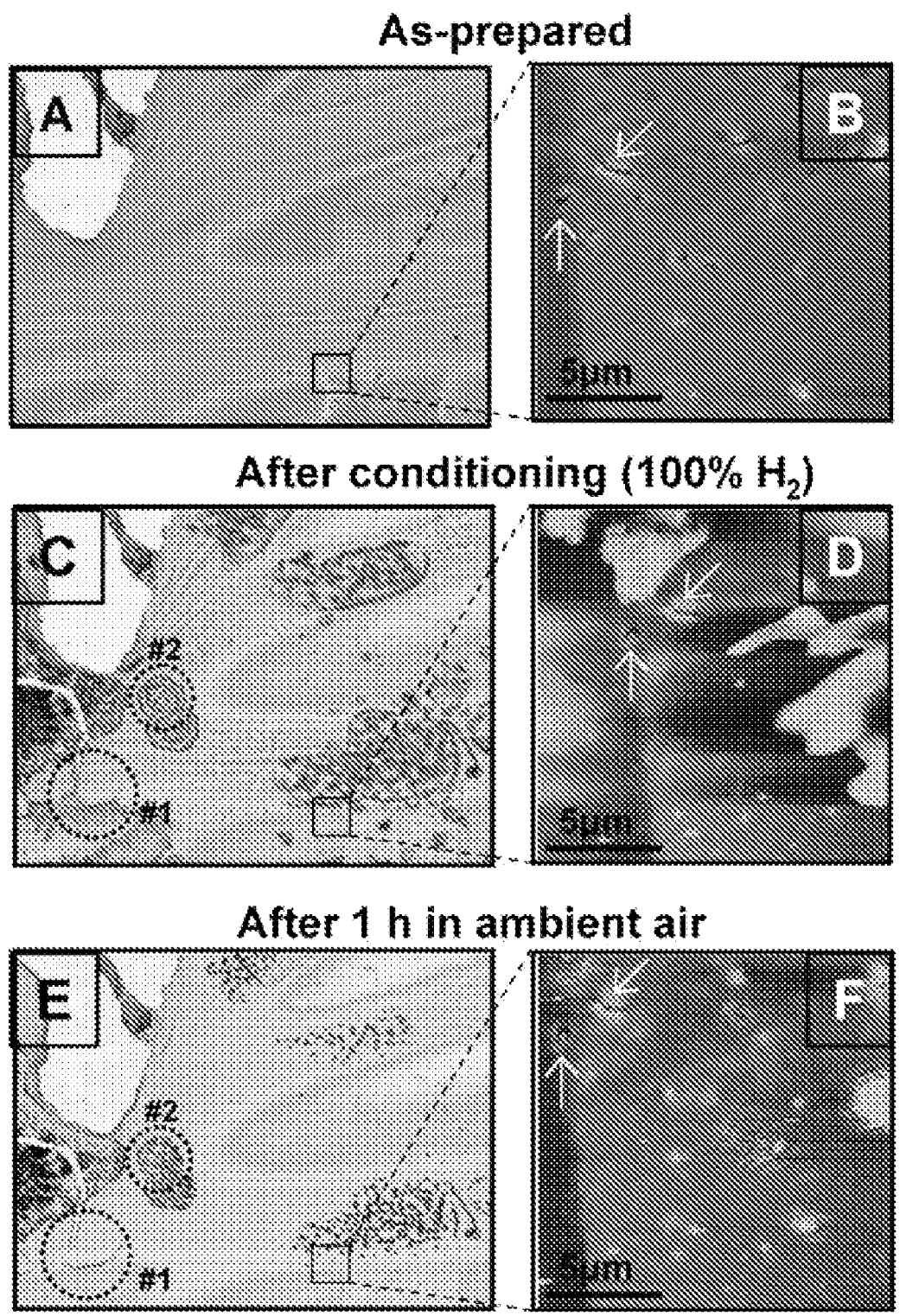
FIGS. 8A-8F are optical microscopy (FIGS. 8A, 8C, 8E) and atomic force microscopy (AFM) (FIGS. 8B, 8D, 8F) images of a film of $C_8H_{17}NH_2$-coated Pd nanoparticles before (FIGS. 8A, 8B) and after (FIGS. 8C, 8D) conditioning by exposure to 100% $H_2$ for 500 s and air for 200 s.

Optical microscopy and atomic force microscopy (AFM) was used to directly image various films before and after exposure to 100% $H_2$ to determine if morphological changes occur during the film conditioning/restructuring process. FIG. 8A shows an optical image and FIG. 8B shows the corresponding AFM image in the same area as indicated by the dashed box of a film of $C_8H_{17}NH_2$-coated Pd nanoparticles drop-cast deposited on an electrode device before any exposure to $H_2$. FIG. 8C and FIG. 8D shows the optical and corresponding AFM image, respectively, of the same area on the same film after exposure to 100% $H_2$ for 500 s, compressed air for 200 s, and ambient air for 5 min during the AFM set-up. The optical image shows a change in the morphology with the appearance of several black features in the image. The corresponding AFM image shows bright features that correlate with these black spots in the optical image, indicating that these are raised features (or islands) that are approximately 100 nm tall that form on top of the surface. The arrows in FIG. 8D are reference points showing the same features on the surface as in FIG. 8B. Morphological changes upon the incorporation of hydrogen into Pd and subsequent removal are appreciated [6]. The morphological changes observed by microscopy are consistent with the 5-6 order of magnitude conductivity increase and 80% loss of $C_8H_{17}NH_2$— ligands from the nanoparticles observed from the I-V curves and surface FTIR data, respectively. FIGS. 8E and 8F show optical and AFM images, respectively, of the same area of the same surface after another 1 h exposure to ambient air. Several of the black features in the optical image and bright features in the AFM image disappeared, showing that there are slow morphological changes that occur in the film over longer periods of time after exposure to $H_2$. Many of the regions appear to heal themselves as indicated by the circle marked #1, but several regions were also altered irreversibly as indicated by the circle marked #2 (FIGS. 8C and 8E).

Figure 9:
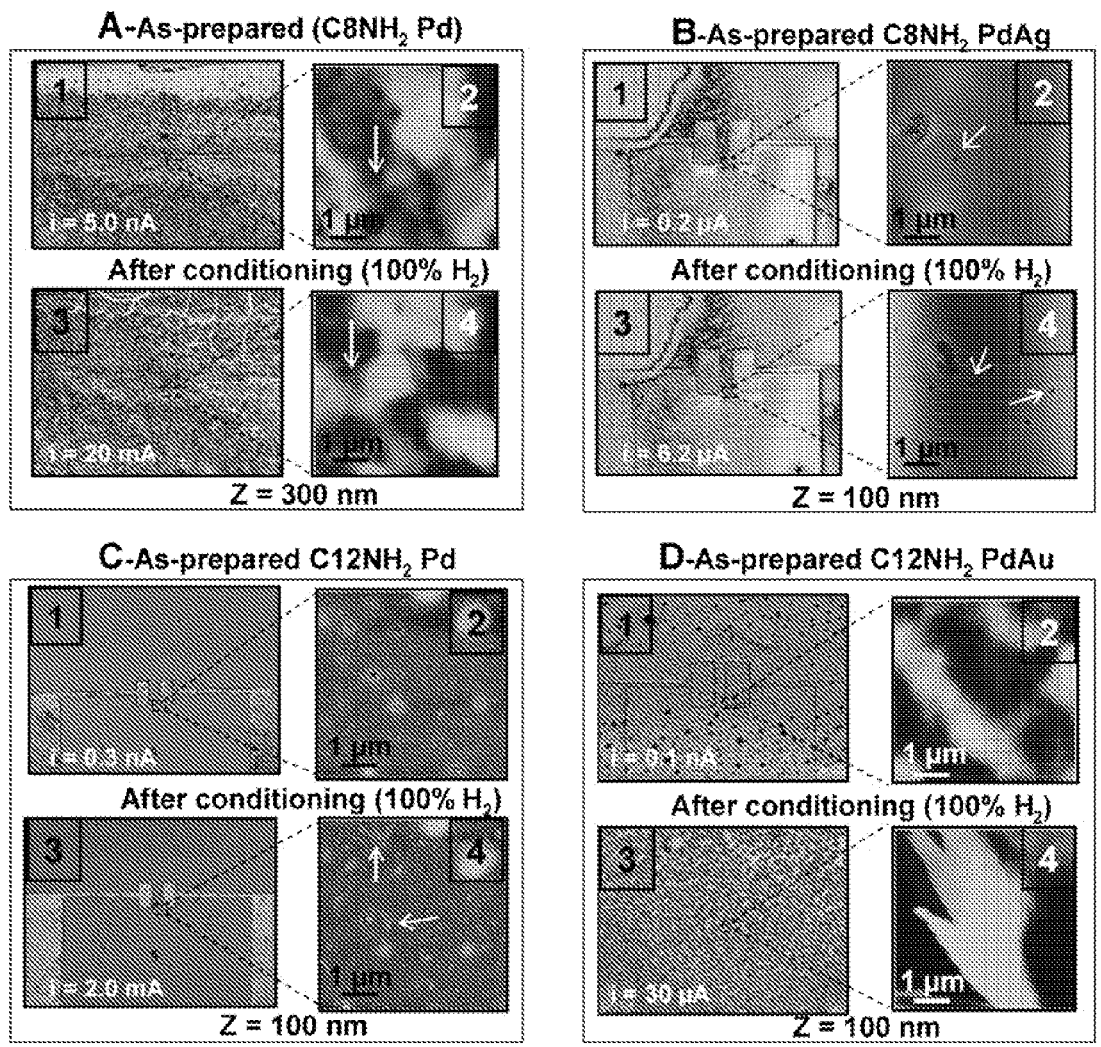
FIGS. 9A-9D are optical microscopy (1, 3) and AFM (2, 4) images of a film before (1, 2) and after (3, 4) conditioning by exposure to 100% $H_2$ for 500 s, 400 s, 800 s, and 300 s for $C_8H_{17}NH_2$-coated Pd (C8 $NH_2$ Pd) (FIG. 9A), $C_8H_{17}NH_2$-coated Pd/Ag (C8 $NH_2$ PdAg) (FIG. 9B), $C_{12}H_{25}NH_2$-coated Pd (C12 NH$_2$ Pd) (FIG. 9C), and C$_{12}$H$_{25}$NH$_2$-coated Pd/Au (C12 NH$_2$ PdAu) (FIG. D) nanoparticles, respectively.

Further AFM and optical microscopy were performed to determine changes in film morphology upon conditioning/restructuring with 100% $H_2$. In order to correlate morphology changes with conductivity changes, alkylamine Pd and Pd alloy nanoparticles were drop-cast deposited between electrodes from a toluene solution containing 70 mg/ml of the nanoparticles and optical and AFM images of the films before and after conditioning were obtained until the electrodes displayed stable currents (indicated on the bottom-left corner of the optical images). AFM images were taken in between the Au electrodes where most of the current flows (dashed rectangles). FIG. 9 shows the optical and corresponding AFM images as indicated by the dashed box of the same area on the same film after exposure to 100% $H_2$. FIG. 9A shows the optical and corresponding AFM image for a film of $C_8H_{17}NH_2$-coated Pd nanoparticles before and after exposure to 100% $H_2$ for 500 s. Frame 9A3 shows cracks on the film (top-right corner) that were not present in Frame 9A1, indicating significant morphology changes during conditioning. Comparison between AFM images in Frames 9A2 and 9A4 show morphology changes on the nanoscale as well. FIG. 9B, Frame 1 shows the optical and corresponding AFM image for a film of $C_8H_{17}NH_2$-coated Pd/Ag nanoparticles before and after exposure to 100% $H_2$ for 400 s. There are no noticeable changes in the optical images (Frames 9B1 and 9B3). There are small changes in the AFM images (Frames 9B2 and 9B4), including the formation of new pits in the image, enlargement of existing pits, and other small changes.

FIG. 9C shows the optical and corresponding AFM image for a film of $C_{12}H_{25}NH_2$-coated Pd nanoparticles before and after exposure to 100% $H_2$ for 800 s. The conditioning time corresponded to the second conditioning event where the current was on the order of $10^{-3}$ A. The optical (Frames 9C1 and 9C3) and AFM images (Frames 9C2 and 9C4) shows minor structural changes during conditioning. FIG. 9D shows the optical and corresponding AFM images for a film of $C_{12}H_{25}NH_2$-coated Pd/Au nanoparticles before and after exposure to 100% $H_2$ for 350 s. The optical images (Frames 9D1 and 9D3) show noticeable morphology changes, including severe roughening of the entire film. The AFM images (Frames 9D2 and 9D4) also show the appearance of large bright regions, which show that this roughening leads to the formation of large islands on the surface.

The optical and AFM images in FIG. 9 are consistent with the conductivity and surface FTIR data obtained on the same films under similar conditions. Films of $C_8H_{17}NH_2$-coated Pd and $C_{12}H_{25}NH_2$-coated Pd/Au nanoparticles showed the largest morphology changes, which is consistent with the large loss of alkyl chains from the surface as determined by FTIR (80 and 62%, respectively) and the large 5-6 order of magnitude increase in current. This shows that loss of the monolayer and large structural changes occur during the large increases in conductivity upon conditioning. Films of $C_8H_{17}NH_2$-coated Pd/Ag and $C_{12}H_{25}NH_2$-coated Pd nanoparticles showed the smallest morphology changes. The small morphology change is consistent with the relatively smaller 4% and 36% loss of the alkyl chains as determined by FTIR for $C_8H_{17}NH_2$-coated Pd/Ag and $C_{12}H_{25}NH_2$-coated Pd nanoparticles, respectively. This is also consistent with the smaller 1-2 order of magnitude increase in current after conditioning for the film of $C_8H_{17}NH_2$-coated Pd/Ag nanoparticles. This is not consistent with the 5-6 order of magnitude current increase for the film of $C_{12}H_{25}NH_2$-coated Pd nanoparticles, however. This shows that film conductivity can increase significantly without noticeable structural changes in the film. Smaller changes can occur below the resolution of the AFM and optical images in FIG. 9. The large increase in conductivity with relatively smaller structural changes can result from the slower kinetics of the film restructuring process. In general, the morphology data in FIG. 9 correlate well with the loss of monolayer determined by FTIR and conductivity changes measured during conditioning.

Example 9

Sensor Comparisons

Figure 10:
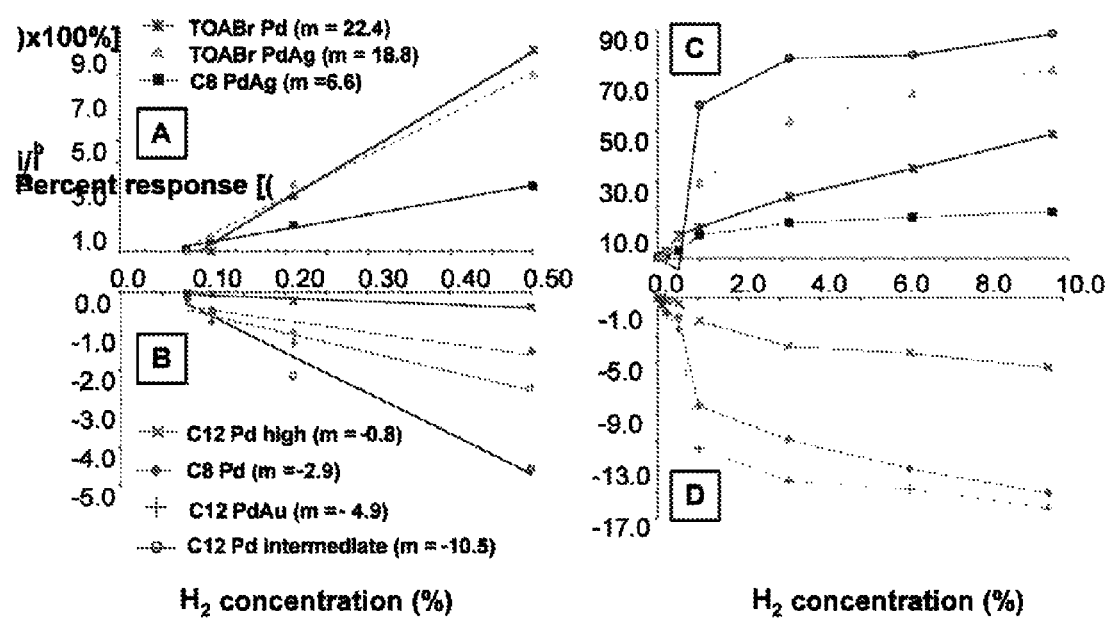
FIGS. 10A-10D are calibration curves showing the percent response versus H$_2$ concentration from 0.00-0.50% (FIGS. 10A, 10B) and 0.0-9.6% (FIGS. 10C, 10D) for C$_{12}$H$_{25}$NH$_2$-coated Pd nanoparticles (C12 Pd) at high current (x) C$_8$H$_{17}$NH$_2$-coated Pd nanoparticles (C8 Pd) (♦), C$_{12}$H$_{25}$NH$_2$-coated Pd/Au nanoparticles (C12 PdAu) (+), and C$_{12}$H$_{25}$NH$_2$-coated Pd nanoparticles (C12 Pd) at an intermediate current (○). The sensors are divided into those that increase in current in the presence of H$_2$ with positive slopes (A, C) and those that decrease in the presence of H$_2$ with negative slopes (B, D). The points on the curves represent the average percent response from three sensor devices at each H$_2$ concentration. The linear regression fits in (A, B) are not forced through the origin and the lines in (C, D) are present as a guide to the eye.

The analytical signal used for the detection of $H_2$ is percent response as described by the following equation:

% Response=$(i_r-i_b)/i_b$*100%=$\Delta i/i_b$*100% where $i_b$ is the initial baseline current in 100% $N_2$, $i_r$ is the current in the presence of $H_2$, and $\Delta i=(i_r-i_b)$. A negative value is equal to a decrease in the current upon exposure to $H_2$. FIG. 10 shows the average calibration curves plotting the % response (y-axis) versus the $H_2$ concentration (x-axis) for the six tested films (not forced through the origin). The points and curves represent the average of three samples. Frames A and B show the response of films whose conductivity increased in the presence of $H_2$ from 0.0 to 0.50% and 0.0 to 9.6% $H_2$, respectively. Frame C and D shows the response of films whose conductivity decreased in the presence of $H_2$ from 0.0 to 0.50% and 0.0 to 9.6% $H_2$, respectively. All the films displayed fairly linear sensing behavior below 0.50% $H_2$. The behavior from 0.0 to 9.6% $H_2$ depended upon the type of stabilizer surrounding the particles. Films of alkylamine-coated nanoparticles exhibited non-linear calibration curves above 0.50% due to the α-β phase transition, which occurs anywhere from 0.3 to 2.0% $H_2$, and saturation of $H_2$ in Pd at higher concentrations [2,6,23].

Films of TOABr-stabilized nanoparticles displayed much more linear behavior over the entire range (more pronounced for TOABr-coated Pd nanoparticles), which is not unexpected since the sensing mechanism is different. The slopes of the linear plots in FIG. 10A reflect the following sensitivity order for films that increase in current: TOABr Pd≈TOABr Pd/Ag>$C_8H_{17}NH_2$ Pd/Ag. The slopes of the linear plots in FIG. 10C reflect the following sensitivity order for films that decrease in current: $C_{12}H_{25}NH_2$ Pd (at intermediate current) (−10.5)>$C_{12}H_{25}NH_2$ Pd/Au (−4.9)>$C_8H_{17}NH_2$ Pd (−2.9)>$C_{12}H_{25}NH_2$ Pd (at high current) (−0.8). All of the films lead to sensor responses below the explosive limit for $H_2$. Films of $C_8H_{17}NH_2$-coated Pd and Pd/Ag nanoparticles exhibited the lowest detection limit (0.08%), while films of $C_{12}H_{25}NH_2$-coated Pd/Au nanoparticles followed by those of $C_8H_{17}NH_2$-coated Pd/Ag silver nanoparticles displayed the fastest response time of 10-15 and 10-20 s, respectively. It is appreciated that Pd/Au and Pd/Ag alloy films show faster response times and greater sensitivity, respectively [25-27]. This is consistent with the present data on $C_{12}H_{25}NH_2$-coated Pd/Au films, which responded very fast during conditioning and also showed the fastest sensor response times (10-15 s). Films of Pd/Au alloys described previously [27] were less sensitive to $H_2$, however, the present films of $C_{12}H_{25}NH_2$-coated Pd/Au nanoparticles were more sensitive compared to films of $C_{12}H_{25}NH_2$-coated pure Pd nanoparticles. Some data sets are <10% RSD. Although the actual percent response measured from sample-to-sample had some deviation, the general trend in sensing behavior was very reproducible. The success column in Table 3 is a measure of the percent success of measuring the indicated $H_2$ concentration for the three samples. All films exhibited 100% success at measuring 0.11% $H_2$, with the exception of TOABr-coated Pd, which is sensitive down to 0.21% $H_2$. Only $C_8H_{17}NH_2$-coated Pd, $C_8H_{17}NH_2$-coated Pd/Ag, and $C_{12}H_{25}NH_2$-coated Pd/Au nanoparticles were sensitive down to 0.08% $H_2$ with 100, 33, and 100% success, respectively.

Table 4 summarizes the overall sensing characteristics of the six different films. The table displays the response direction (current increase or decrease), limit of detection, percent response measured at 1% $H_2$, and range of response times for 3 different samples of each type of film.

TABLE 3

Complete data showing % response as a function of H$_2$ concentration for all the three sensors measured for each type of film involved in this study.

| % H$_2$ | sample 1 % response | sample 2 % response | sample 3 % response | AVG | STD | % RSD | % success |
|---|---|---|---|---|---|---|---|
| C8NH$_2$ Pd | | | | | | | |
| 0.08 | −0.2 | −0.2 | −0.2 | −0.2 | 0.02 | 9.4 | 100% |
| 0.11 | −0.5 | −0.5 | −0.4 | −0.5 | 0.09 | 19.4 | 100% |
| 0.21 | −1.0 | −1.5 | −0.6 | −1.0 | 0.45 | 43.2 | 100% |
| 0.50 | −1.5 | −2.3 | −0.8 | −1.5 | 0.77 | 50.3 | 100% |
| 1.00 | −8.8 | −10.0 | −4.3 | −7.7 | 3.01 | 39.1 | 100% |
| 3.15 | −10.8 | −13.9 | −8.3 | −11.0 | 2.78 | 25.4 | 100% |
| 6.20 | −12.2 | −16.3 | −11.1 | −13.2 | 2.76 | 21.0 | 100% |
| 9.60 | −15.5 | −17.6 | −12.0 | −15.0 | 2.84 | 18.9 | 100% |
| C8NH$_2$ PdAg | | | | | | | |
| 0.08 | 0.0 | 0.2 | 0.0 | 0.1 | 0.13 | 173.2 | 33% |
| 0.11 | 0.5 | 0.6 | 0.4 | 0.5 | 0.10 | 20.4 | 100% |
| 0.21 | 1.0 | 1.7 | 0.9 | 1.2 | 0.45 | 38.2 | 100% |
| 0.50 | 3.6 | 3.6 | 1.6 | 3.0 | 1.15 | 39.0 | 100% |
| 1.00 | 6.9 | 9.6 | 10.5 | 9.0 | 1.89 | 21.0 | 100% |
| 3.15 | 11.0 | 15.2 | 15.3 | 13.9 | 2.49 | 18.0 | 100% |
| 6.20 | 12.8 | 18.3 | 16.9 | 16.0 | 2.88 | 18.1 | 100% |
| 9.60 | 15.7 | 20.1 | 18.8 | 18.2 | 2.24 | 12.3 | 100% |
| C12NH$_2$ Pd (intermediate currents) | | | | | | | |
| 0.08 | 0.0 | 0.0 | 0.0 | 0.0 | 0.00 | 0.0 | 0% |
| 0.11 | −0.5 | −0.7 | −0.3 | −0.5 | 0.21 | 41.2 | 100% |
| 0.21 | −2.6 | −2.4 | −1.4 | −2.2 | 0.63 | 29.3 | 100% |
| 0.50 | −4.0 | −4.7 | −5.0 | −4.6 | 0.51 | 11.2 | 100% |
| 1.00 | 69.2 | 44.5 | 67.7 | 60.5 | 13.86 | 22.9 | 100% |
| 3.15 | 80.7 | 82.2 | 73.2 | 78.7 | 4.84 | 6.2 | 100% |
| 6.20 | 83.9 | 86.7 | 69.8 | 80.1 | 9.07 | 11.3 | 100% |
| 9.60 | 85.1 | 95.2 | 85.4 | 88.6 | 5.74 | 6.5 | 100% |
| C12NH$_2$ Pd (high currents) | | | | | | | |
| 0.08 | 0.0 | 0.0 | 0.0 | 0.0 | 0.00 | 0.0 | 0% |
| 0.11 | −0.1 | 0.0 | 0.0 | 0.0 | 0.01 | 0.0 | 33% |
| 0.21 | −0.3 | −0.3 | −0.1 | −0.2 | 0.10 | 45.9 | 100% |
| 0.50 | −0.4 | −0.4 | −0.3 | −0.4 | 0.06 | 16.4 | 100% |
| 1.00 | −1.8 | −1.9 | −3.2 | −2.3 | 0.78 | 34.0 | 100% |
| 3.15 | −3.2 | −4.9 | −3.2 | −3.8 | 0.98 | 26.1 | 100% |
| 6.20 | −3.6 | −5.7 | −3.5 | −4.3 | 1.26 | 29.6 | 100% |
| 9.60 | −4.0 | −8.4 | −3.7 | −5.4 | 2.65 | 49.5 | 100% |
| C12NH$_2$ PdAu | | | | | | | |
| 0.08 | −0.1 | −0.1 | −0.2 | −0.2 | 0.06 | 39.8 | 100% |
| 0.11 | −0.4 | −0.9 | −0.9 | −0.7 | 0.33 | 44.7 | 100% |
| 0.21 | −0.6 | −1.8 | −1.5 | −1.3 | 0.67 | 51.4 | 100% |
| 0.50 | −1.5 | −2.8 | −3.1 | −2.5 | 0.84 | 34.4 | 100% |
| 1.00 | −7.0 | −11.6 | −14.7 | −11.1 | 3.87 | 34.9 | 100% |
| 3.15 | −11.8 | −14.2 | −16.4 | −14.1 | 2.32 | 16.4 | 100% |
| 6.20 | −13.1 | −14.3 | −17.0 | −14.8 | 1.96 | 13.2 | 100% |
| 9.60 | −16.1 | −15.0 | −17.5 | −16.2 | 1.25 | 7.7 | 100% |
| TOABr Pd | | | | | | | |
| 0.08 | 0.0 | 0.0 | 0.0 | 0.0 | 0.00 | 0.0 | 0% |
| 0.11 | 0.0 | 0.0 | 0.0 | 0.0 | 0.00 | 0.0 | 0% |
| 0.21 | 2.3 | 2.7 | 2.6 | 2.5 | 0.20 | 7.9 | 100% |
| 0.50 | 6.9 | 9.4 | 11.1 | 9.1 | 2.08 | 22.9 | 100% |
| 1.00 | 13.0 | 9.2 | 13.9 | 12.0 | 2.51 | 20.9 | 100% |
| 3.15 | 26.5 | 21.0 | 25.0 | 24.2 | 2.85 | 11.8 | 100% |
| 6.20 | 40.0 | 31.0 | 35.1 | 35.4 | 4.51 | 12.7 | 100% |
| 9.60 | 54.8 | 46.0 | 46.1 | 49.0 | 5.07 | 10.4 | 100% |
| TOABr PdAg | | | | | | | |
| 0.08 | 0.0 | 0.0 | 0.0 | 0.0 | 0.00 | 0.0 | 0% |
| 0.11 | 0.6 | 0.7 | 0.7 | 0.7 | 0.06 | 8.1 | 100% |
| 0.21 | 3.7 | 2.1 | 3.4 | 3.1 | 0.88 | 28.6 | 100% |
| 0.50 | 11.3 | 4.5 | 8.3 | 8.0 | 3.38 | 42.2 | 100% |
| 1.00 | 32.5 | 28.9 | 27.1 | 29.5 | 2.74 | 9.3 | 100% |
| 3.15 | 60.9 | 50.9 | 50.4 | 54.0 | 5.91 | 10.9 | 100% |
| 6.20 | 70.0 | 62.5 | 62.7 | 65.0 | 4.32 | 6.6 | 100% |
| 9.60 | 78.2 | 71.4 | 74.6 | 74.7 | 3.43 | 4.6 | 100% |

TABLE 4

Sensing characteristics of six tested films.

| | Limit of detection (% H$_2$) | | | Percent Response at 1.0% H$_2$ | | | Response time at 1.0% H$_2$ (s) |
|---|---|---|---|---|---|---|---|
| | S#1 | S#2 | S#3 | S#1 | S#2 | S#3 | |
| Type of sensor response direction = increase in current | | | | | | | |
| TOABr Pd | 0.21 | 0.21 | 0.21 | 13.0 | 9.2 | 13.9 | 40-55 |
| TOABr Pd/Ag | 0.11 | 0.11 | 0.11 | 32.5 | 28.9 | 27.1 | 60-70 |
| C$_8$NH$_2$ Pd/Ag | 0.11 | 0.08 | 0.11 | 6.9 | 9.6 | 10.5 | 10-20 |
| C$_{12}$NH$_2$ Pd (medium current) | 0.11 | 0.11 | 0.11 | 69.2 | 44.5 | 67.7 | 50-90 |
| Type of sensor response direction = decrease in current | | | | | | | |
| C$_8$NH$_2$ Pd | 0.08 | 0.08 | 0.08 | −8.8 | −10.0 | −4.3 | 20-30 |
| C$_{12}$NH$_2$ Pd (high current) | 0.11 | 0.11 | 0.11 | −1.8 | −1.9 | −3.2 | 10-20 |
| C$_{12}$NH$_2$ Pd/Au | 0.08 | 0.08 | 0.08 | −7.0 | −11.6 | −14.7 | 10-15 |

The foregoing examples demonstrate the hydrogen reactivity of drop-cast films of chemically-synthesized alkylamine-coated Pd, Pd/Ag (10:1) and Pd/Au (10:1) nanoparticles and films of tetraoctylammonium bromide (TOABr)-stabilized Pd and Pd/Ag (10:1) nanoparticles. The as-prepared films are highly reactive to H$_2$ and do not require O$_3$ or thermal treatment as previously observed for films of C$_6$H$_{13}$S-coated Pd nanoparticles. The films can be placed into two categories; those that decrease in current in the presence of H$_2$ and those that increase. Films of C$_8$H$_{17}$NH$_2$-coated Pd nanoparticles, C$_{12}$H$_{25}$NH$_2$-coated Pd nanoparticles (second conditioning), and C$_{12}$H$_{25}$NH$_2$-coated Pd/Au nanoparticles exhibit large 5-6 order of magnitude irreversible increases in current upon the first exposure to 100% H$_2$, which is accompanied by a large loss of the alkylamine monolayer and noticeable morphological changes in the case of C$_{12}$H$_{25}$NH$_2$-coated Pd nanoparticle films. After this irreversible conditioning/restructuring, the films exhibit stable, reversible decreases in current in the presence of H$_2$ concentrations down to 0.08%. Films of C$_{12}$H$_{25}$NH$_2$-coated Pd (first conditioning) and C$_{12}$H$_{25}$NH$_2$-coated Pd/Ag nanoparticles exhibit a much smaller 1-2 order of magnitude irreversible increase in current upon the first exposure to 100% H$_2$, which is accompanied by very little loss of the alkylamine monolayer and correspondingly small morphological changes in the film.

Further, after this irreversible conditioning/restructuring, the films exhibit reversible increases in current in the presence of $H_2$ concentrations down to 0.08%, which is stable for the case of coated Pd/Ag nanoparticles. Films comprised of TOABr-coated Pd and Pd/Ag nanoparticles exhibit reversible, stable increases in current in the presence of $H_2$ concentrations down to 0.11% without any pre-treatment or conditioning. Alkylamine-coated Pd nanoparticles change in current through higher resistance of PdHx or lower resistance during volume increases of PdHx and the sensing mechanism of ammonium-coated Pd nanoparticles shows ionic conductivity. All of the films are easy to synthesize on a large scale and the devices are easy to construct, leading to responses to $H_2$ below the explosive limit.

REFERENCES

Throughout this application, various publications are referenced. All such references are incorporated herein by reference, including the references set forth in the following list.

[1] Ramachandran, R.; Menon, R. K. *Int. J. Hydrogen Energy* 1998, 23, 593-598.
[2] Christofides, C.; Mandelis, A. *J. Appl. Phys.* 1990, 68, 1-30.
[3] Che, G.; Lakshmi, B. B.; Fisher, E. R.; Martin, C. R. *Nature* 1998, 393, 346-349.
[4] Schalpbach, L.; Zuttel, A. *Nature* 2001, 414, 353-358.
[5] Horonouchi, S.; Yamanoi, Y.; Yonezawa, T.; Mouri, T.; Nishihara, H. *Langmuir* 2006, 22, 1880-1884.
[6] Lewis, F. A. *The Palladium/Hydrogen System*; Academic Press Inc.: London, 1967.
[7] Sakamoto, Y.; Takai, K.; Takashima, I.; Imada, M. *J. Phys.: Condens. Matter* 1996, 8, 3399-3411.
[8] Yu, S.; Welp, U.; Hua, L. Z.; Rydh, A.; Kwok, W. K.; Wang, H. H. *Chem. Mater.* 2005, 17, 3445-3450.
[9] Favier, F.; Walter, E. C.; Zach, M. P.; Benter, T.; Penner, R. M. *Science* 2001, 293, 2227-2231.
[10] Walter, E. C.; Favier, F.; Penner, R. M. *Anal. Chem.* 2002, 74, 1546-1553.
[11] Dankert, O.; Pundt, A. *Appl. Phys. Lett.* 2002, 81, 1618-1620.
[12] Xu, T.; Zach, M. P.; Xiao, Z. L.; Rosenmann, D.; Welp, U.; Kwok, W. K.; Crabtree, G. W. *Appl. Phys. Lett.* 2005, 86, 203104.
[13] Yun, M.; Myung, N. V.; Vasquez, R. P.; Lee, C.; Menke, E.; Penner, R. M. *Nano Lett.* 2004, 4, 419-422.
[14] Kaltenpoth, G.; Schnabel, P.; Menke, E.; Walter, E. C.; Grunze, M.; Penner, R. M. *Anal. Chem.* 2003, 75, 4756-4765.
[15] Im, Y.; Lee, C.; Vazquez, R. P.; Bangar, M. A.; Myung, N. V.; Menke, E. J.; Penner, R. M.; Yun, M. *Small* 2006, 2, 356-358.
[16] Luongo, K.; Sine, A.; Bhansali, S. *Sens. Actuators B* 2005, 111-112, 125-129.
[17] Morris, J. E.; Kiesow, A.; Hong, M.; Wu, F. *Int. J. Electronics* 1996, 81, 441-447.
[18] Ibañez, F. J.; Zamborini, F. P. *Langmuir* 2006, 22, 9789-9796.
[19] Bévenot, X.; Trouillet, A.; Veillas, C.; Gagnaire, H.; Clement, M. *Sens. Actuators B* 2000, 67, 57-67.
[20] Garcia, J. A.; Mandelis, A. *Rev. Sci. Instrum.* 1996, 67, 3981-3983.
[21] Kalli, K.; Othonos, A.; Christofides, C. *Rev. Sci. Instrum.* 1998, 69, 3331-3338.
[22] Kalli, K.; Othonos, A.; Christofides, C. *J. Appl. Phys.* 2002, 91, 3829-3840.
[23] Lin, H.; Gao, T.; Fantini, J.; Sailor, M. J. *Langmuir* 2004, 20, 5104-5108.
[24] Smith, A. L.; Shirazi, H. M. *Thermochim. Acta* 2005, 432, 202-211.
[25] Zhao, Z.; Carpenter, M. A. *J. Appl. Phys.* 2005, 97, 124301.
[26] Zhao, Z.; Carpenter, M. A.; Xia, H.; Welch, D. *Sens. Actuators B* 2006, 113, 532-538.
[27] Zhao, Z.; Carpenter, M. A.; Welch, D.; Xia, H. *Anal. Chem.* 2004, 76, 6321-6326.
[28] Dwivedi, D.; Dwivedi, R.; Srivastava, S. K. *Sens. Actuators B* 2000, 71, 161-168.
[29] Huang, L.; Gong, H.; Peng, D.; Meng, G. *Thin Solid Films* 1999, 345, 217-221.
[30] Hughes, R. C.; Schübert, W. K. *J. Appl. Phys.* 1992, 71, 542-544.
[31] Hughes, R. C.; Schübert, W. K.; Zipperian, T. E.; Rodriguez, J. L.; Plut, T. A. *J. Appl. Phys.* 1987, 62, 1074-1083.
[32] Kang, W. P.; Gurbuz, Y. *J. Appl. Phys.* 1994, 75, 8175-8181.
[33] Kolmakov, A.; Klenov, D. O.; Lilach, Y.; Stemmer, S.; Moskovits, M. *Nano Lett.* 2005, 5, 667-673.
[34] Kong, J.; Chapline, M. G.; Dai, H. *Adv. Mater.* 2001, 13, 1384-1386.
[35] Lutz, B. J.; Fan, Z. H. *Anal. Chem.* 2005, 77, 4969-4975.
[36] Mizsei, J.; Voutilainen, J.; Saukko, S.; Lantto, V. *Thin Solid Films* 2001, 391, 209-215.
[37] Sayago, I.; Terrado, E.; Lafuente, E.; Horrillo, M. C.; Maser, W. K.; Benito, A. M.; Navarro, R.; Urriolabeitia, E. P.; Martinez, M. T.; Gutierrez, J. *Synthetic Metals* 2005, 148, 15-19.
[38] Wolfe, D. B.; Love, J. C.; Paul, K. E.; Chabinyc, M. L.; Whitesides, G. M. *Appl. Phys. Lett.* 2002, 80, 2222-2224.
[39] Xia, Y.; Whitesides, G. M. *Polym. Mater. Sci. Eng.* 1997, 77, 596.
[40] Brust, M.; Walker, M.; Bethell, D.; Schiffrin, D. J.; Whyman, R. *Chem. Comm.* 1994, 7, 801-802.
[41] Ibañez, F. J.; Zamborini, F. P. *Langmuir* 2006, 22, 9789-9796.
[42] Zamborini, F. P.; Gross, S. M.; Murray, R. W. *Langmuir* 2001, 17, 481-487.
[43] Leff, D. V.; Brandt, L.; Heath, J. R. *Langmuir* 1996, 12, 4723-4730.
[44] Isaacs, S. R.; Culter, E. C.; Park, J.-S.; Lee, T. R.; Shon, Y.-S. *Langmuir.* 2005, 21, 5689-5692
[45] Zamborini, F. P.; Leopold, M. C.; Hicks, J. F.; Kulesza, P. J.; Malik, M. A.; Murray, R. W. *J. Am. Chem. Soc.* 2002, 124, 8958-8964.
[46] Terrill, R. H.; Postlethwaite, T. A.; Chen, C.-h.; Poon, C.-D.; Terzis, A.; Chen, A.; Hutchison, J. E.; Clark, M. R.; Wignall, G.; Londono, J. D.; Superfine, R.; Falvo, M.; Johnson Jr., C. S.; Samulski, E. T.; Murray, R. W. *J. Am. Chem. Soc.* 1995, 117, 12537-12548.
[47] Zamborini, F. P.; Smart, L. E.; Leopold, M. C.; Murray, R. W. *Anal. Chim. Acta* 2003, 496, 3-16.
[48] Wuelfing, W. P.; Green, S. J.; Pietron, J. J.; Cliffel, D. E.; Murray, R. W. *J. Am. Chem. Soc.* 2000, 122, 11465-11472.
[49] Ibañez, F. J.; Zamborini, F. P. *Langmuir* 2006, 22, 9789-9796.
[50] Choi, J.-P.; Coble, M. M.; Branham, M. R.; DeSimone, J. M.; Murray, R. W. *J. Phys. Chem. C* 2007, 111, 3778-3785
[51] Rao, C. R. K.; Lakshminarayanan, V.; Trivedi, D. C. *Materials Letters* 2006, 60, 3169.
[52] Sachtler, W. M. H.; Huang, Y. *Applied Catalysis A* 1999, 182, 365-378.
[53] Pavia, D. L.; Lampman, G. M.; Kriz, G. S. *Introduction to Spectroscopy*; Harcout Brace College: New York, 1996.

[54] Hostetler, M. J.; Zhong, C.-J.; Yen, B. K. H.; J, A.; Gross, S. M.; Evans, N. D.; Porter, M.; Murray, R. W. JACS 1998, 120, 9396-9397.

It will be understood that various details of the presently-disclosed subject matter can be changed without departing from the scope of the subject matter disclosed herein. Furthermore, the foregoing description is for the purpose of illustration only, and not for the purpose of limitation.

What is claimed is:

1. A sensor for detecting hydrogen, comprising:
an electrically insulating support;
at least two electrodes positioned at a distance from one another and affixed to the support; and
a chemiresistant film deposited at least between said electrodes and comprising alkylamine-coated palladium nanoparticles or alkylamine-coated palladium alloy nanoparticles, wherein the alkylamine-coated palladium nanoparticles or alkylamine-coated palladium alloy nanoparticles increase the conductivity of the chemiresistant film upon exposure to hydrogen.

2. The sensor of claim 1, wherein the support and the electrodes are inert to hydrogen.

3. The sensor of claim 1, wherein the distance between the electrodes is from about 100 nanometers to about 1 millimeter.

4. The sensor of claim 1, wherein the distance between the electrodes is about 23 micrometers.

5. The sensor of claim 1, wherein the palladium alloy is selected from the group consisting of a palladium/gold alloy and a palladium/silver alloy.

6. The sensor of claim 1, wherein the alkylamine is a compound of Formula I:

$$CH_3(CR_1R_2)_n(NR_3R_4)— \qquad (I)$$

wherein n is an integer from 3 to 15; and $R_1$, $R_2$, $R_3$, and $R_4$ are each independently selected from the group consisting of H, alkyl, and substituted alkyl.

7. The sensor of claim 6, wherein the alkylamine is selected from the group consisting of $C_6H_{13}NH_2$—, $C_8H_{17}NH_2$—, and $C_{12}H_{25}NH_2$—.

8. The sensor of claim 1, wherein the conductivity is reversible.

9. The sensor of claim 1, wherein the chemiresistant film further comprises alkylthiolate-coated palladium nanoparticles or alkylthiolate-coated palladium alloy nanoparticles.

10. The sensor of claim 9, wherein the alkylthiolate is a compound of formula II:

$$CH_3(CR_1R_2)_nS— \qquad (II)$$

wherein n is an integer from 3 to 15; and $R_1$ and $R_2$ are each independently selected from the group consisting of H, alkyl, and substituted alkyl.

11. The sensor of claim 10, wherein the alkylthiolate is $C_6H_{13}S$—.

12. The sensor of claim 9, wherein the palladium alloy is selected from the group consisting of a palladium/gold alloy and a palladium/silver alloy.

13. The sensor of claim 1, wherein the chemiresistant film is drop-cast deposited at least between the at least two electrodes.

14. The sensor of claim 1, wherein the chemiresistant film is micro-contact printed at least between the at least two electrodes.

15. A method of detecting hydrogen in a sample, comprising:
providing a sensor including:
an electrically insulating support;
at least two electrodes positioned at a distance from one another and affixed to the support; and
a chemiresistant film deposited at least between said electrodes and comprising alkylamine-coated palladium nanoparticles or alkylamine-coated palladium alloy nanoparticles, wherein the alkylamine-coated palladium nanoparticles or alkylamine-coated palladium alloy nanoparticles increase the conductivity of the chemiresistant film upon exposure to hydrogen;
applying a voltage potential between the at least two electrodes;
exposing the sensor to a gas sample; and
detecting a change in current between the at least two electrodes to thereby detect hydrogen in the sample.

16. The method of claim 15, wherein the hydrogen is present in the gas sample at a concentration of at least about 0.08%.

17. The method of claim 15, wherein the hydrogen is present in the gas sample at a concentration of about 9.6% to about 0.08%.

18. A sensor for detecting hydrogen, comprising:
an electrically insulating support;
at least two electrodes positioned at a distance from one another and affixed to the support; and
a chemiresistant film deposited at least between the electrodes and comprising surfactant-coated palladium nanoparticles or surfactant-coated palladium alloy nanoparticles, wherein the surfactant is a compound of Formula (III):

$$[CH_3(CR_1R_2)_n]_4NR_3 \qquad (III)$$

wherein n is an integer from 3 to 15; $R_1$ and $R_2$ are each independently selected from the group consisting of H, alkyl, or substituted alkyl; and, $R_3$ is selected from the group consisting of $Cl^-$, $I^-$, $NO_3^-$, $SO_4^{2-}$, $ClO_4^{2-}$, and $PF_6^-$; and
wherein the surfactant-coated palladium nanoparticles or surfactant-coated palladium alloy nanoparticles increase the conductivity of the chemiresistant film upon exposure to hydrogen.

19. The sensor of claim 18, wherein the surfactant is tetraoctylammonium bromide (TOABr).

20. The sensor of claim 18, wherein the support and the electrodes are inert to hydrogen.

21. The sensor of claim 18, wherein the distance between the electrodes is from about 100 nm to about 1 mm.

22. The sensor of claim 18, wherein the distance between the electrodes is about 23 micrometers.

23. The sensor of claim 18, wherein the palladium alloy is a palladium/silver alloy.

24. The sensor of claim 18, wherein the conductivity is reversible.

25. The sensor of claim 18, wherein the chemiresistant film is drop-cast deposited at least between the at least two electrodes.

26. The sensor of claim 18, wherein the chemiresistant film is micro-contact printed at least between the at least two electrodes.

27. A method of detecting hydrogen in a sample, comprising:
provviding a sensor including:
an electrically insulating support;
at least two electrodes positioned at a distance from one another and affixed to the support; and
a chemiresistant film deposited at least between the electrodes and comprising surfactant-coated palladium nanoparticles or surfactant-coated palladium alloy nanoparticles, wherein the surfactant is a compound of Formula (III):

$$[CH_3(CR_1R_2)_n]_4NR_3 \quad (III)$$

wherein n is an integer from 3 to 15; $R_1$ and $R_2$ are each independently selected from the group consisting of H, alkyl, or substituted alkyl; and, $R_3$ is selected from the group consisting of $Cl^-$, $I^-$, $NO_3^-$, $SO_4^{2-}$, $ClO_4^{2-}$, and $PF_6^-$; and wherein the surfactant-coated palladium nanoparticles or surfactant-coated palladium alloy nanoparticles increase the conductivity of the chemiresistant film upon exposure to hydrogen;
applying a voltage potential between the at least two electrodes;
exposing the sensor to a gas sample; and
detecting a change in current between the at least two electrodes to thereby detect hydrogen in the sample.

28. The method of claim 27, wherein the hydrogen is present in the gas sample at a concentration of at least about 0.08%.

29. The method of claim 27, wherein the hydrogen is present in the gas sample at a concentration of about 9.6% to about 0.08%.

* * * * *